(12) United States Patent
Chen et al.

(10) Patent No.: US 10,604,493 B2
(45) Date of Patent: *Mar. 31, 2020

(54) COMPOSITIONS, METHODS OF USE, AND METHODS OF TREATMENT

(71) Applicants: University of South Florida, Tampa, FL (US); The Regents of the University of California, Oakland, CA (US)

(72) Inventors: Yu Chen, Tampa, FL (US); Derek Nichols, Tampa, FL (US); Adam R. Renslo, Oakland, CA (US); Priyadarshini Jaishankar, Newark, CA (US); Erica M. W. Lauterwasser, Hessheim (DE)

(73) Assignees: University of South Florida, Tampa, FL (US); The Regents of the University of California, Oakland, CA (US)

(*) Notice: Subject to any disclaimer, the term of this patent is extended or adjusted under 35 U.S.C. 154(b) by 57 days.

This patent is subject to a terminal disclaimer.

(21) Appl. No.: 15/345,619

(22) Filed: Nov. 8, 2016

(65) Prior Publication Data

US 2017/0088524 A1  Mar. 30, 2017

Related U.S. Application Data

(63) Continuation of application No. 14/370,715, filed as application No. PCT/US2013/020212 on Jan. 4, 2013, now Pat. No. 9,556,131.

(Continued)

(51) Int. Cl.
*C07D 257/04* (2006.01)
*C07D 403/12* (2006.01)

(Continued)

(52) U.S. Cl.
CPC ............ *C07D 257/04* (2013.01); *A61K 31/41* (2013.01); *A61K 31/416* (2013.01);
(Continued)

(58) Field of Classification Search
CPC .... C07D 257/04; C07D 403/12; A61K 31/41; A61K 31/416; A61K 31/4184; A61K 45/06; Y02A 50/473; Y02A 50/481
See application file for complete search history.

(56) References Cited

U.S. PATENT DOCUMENTS 5,049,572 A     9/1991  Scherrer et al.
2006/0135589 A1  6/2006  Berdino et al.
(Continued)

FOREIGN PATENT DOCUMENTS

EP    0816329    1/1998
EP    1534717    6/2005
(Continued)

OTHER PUBLICATIONS

Kubinyi (3D QSAR in Drug Design: Ligand-Protein Interactions and Molecular Similarity, vol. 2-3, Springer, 1998, 800 pages. p. 243-44 provided.*

(Continued)

*Primary Examiner* — Robert H Havlin
(74) *Attorney, Agent, or Firm* — Fish & Richardson P.C.

(57) ABSTRACT

Embodiments of the present disclosure, in one aspect, relate to a beta-lactamase inhibitor, pharmaceutical compositions including a beta-lactamase inhibitor, methods of treatment of a condition (e.g., infection) or disease, methods of treatment using compositions or pharmaceutical compositions, and the like.

10 Claims, 8 Drawing Sheets

Related U.S. Application Data

(60) Provisional application No. 61/583,679, filed on Jan. 6, 2012.

(51) Int. Cl.
| | |
|---|---|
| *A61K 31/4184* | (2006.01) |
| *A61K 31/41* | (2006.01) |
| *A61K 31/416* | (2006.01) |
| *A61K 45/06* | (2006.01) |

(52) U.S. Cl.
CPC .......... *A61K 31/4184* (2013.01); *A61K 45/06* (2013.01); *C07D 403/12* (2013.01); *Y02A 50/473* (2018.01); *Y02A 50/481* (2018.01)

(56) References Cited

U.S. PATENT DOCUMENTS

| | | |
|---|---|---|
| 2007/0105899 A1 | 5/2007 | Suzuki et al. |
| 2010/0317621 A1 | 12/2010 | Burns et al. |

FOREIGN PATENT DOCUMENTS

| | | |
|---|---|---|
| JP | S5746971 | 3/1982 |
| JP | H01261379 | 10/1989 |
| JP | 2009510170 | 3/2009 |
| KR | 1020010033621 | 4/2001 |
| KR | 1020100130176 | 12/2010 |
| WO | 9009989 | 9/1990 |
| WO | 9316053 | 8/1993 |
| WO | 9704775 | 2/1997 |
| WO | 0198274 | 12/2001 |
| WO | 2007117465 | 10/2004 |
| WO | 2008048991 | 4/2008 |
| WO | 2009038842 | 3/2009 |
| WO | 2009091856 | 7/2009 |
| WO | 2011026107 | 3/2011 |

OTHER PUBLICATIONS

Wermuth, The Practice of Medicinal Chemistry, 2d ed. (2003), 768 pages. Chs. 9-10 provided.*
Patani et al. (Chem. Rev. 1996, 96, 3147-3176).*
Smart (J. Fluorine Chemistry, 109 (2001), p. 3-11).*
Registry (Registry entry 326903-68-8, Entered: Mar. 13, 2001).*
Thornber (Chem. Soc. Rev., 1979, v. 8, p. 563-580).*
Baures et al., "Synthesis and Evaluation of Inhibitors of Transthyretin Amyloid Formation Based on the Non-steroidal Anti-inflammatory Drug, Flufenamic Acid." Department of Chemistry and The Skaggs Institute of Chemical Biology, The Scripps Research Institute, 10550 North Torrey Pines Road, MB12, La Jolla, CA 92037, USA; 9 pages.
Bennett et al. "Molecular basis of beta-lactamase induction in bacteria." Antimicrob Agents Chemother 1993, 37, 153-8.
Bethel et al., "Exploring the Inhibition of CTX-M-9 by—Lactamase Inhibitors and Carbapenems", Antimicrobial Agents and Chemotherapy, vol. 55, No. 7, May 9, 2011 (May 9, 2011), pp. 3465-3475.
Bonnet, "Growing group of extended-spectrum beta-lactamases: the CTX-M enzymes." Antimicrob Agents Chemother 2004, 48, 1-14.
Bradford, "Extended-spectrum beta-lactamases in the 21st century: characterization, epidemiology, and detection of this important resistance threat." Clin Microbiol Rev 2001, 14, 933-51.
Bush et al., "A functional classification scheme for beta-lactamases and its correlation with molecular structure." Antimicrob Agents Chemother 1995, 39, 1211-33.
Chen et al., "Atomic resolution structures of CTX-M beta-lactamases: extended spectrum activities from increased mobility and decreased stability." J Mol Biol 2005, 348, 349-62.
Chen et al., "Crystal structures of penicillin-binding protein 6 from *Escherichia coli*." J Am Chem Soc 2009, 131, 14345-54.
Chen et al., "Molecular docking and ligand specificity in fragment-based inhibitor discovery." Nat Chem Biol 2009, 5, 358-64.
Chen et al., "Structure, function, and inhibition along the reaction coordinate of CTX-M beta-lactamases." J Am Chem Soc 2005, 127, 5423-34.
Chen et al., "The acylation mechanism of CTX-M beta-lactamase at 0.88 a resolution." J Am Chem Soc. 2007, 129, 5378-80.
Collaborative Computational Project, N. The CCP4 suite: programs for protein crystallography. Acta Crystallogr D Biol Crystallogr 1994, 50, 760-763.
Delmas et al., "Structural insights into substrate recognition and product expulsion in CTX-M enzymes." J Mol Biol 400, 108-20.
Drawz et al., "Three decades of beta-lactamase inhibitors." Clin Microbial Rev 2010, 23, 160-201.
Emsley et al., "Coot: model-building tools for molecular graphics." Acta Crystallogr D Biol Crystallogr. 2004, 60, 2126-32.
Frere, "Beta-lactamases and bacterial resistance to antibiotics." Mol Microbiol 1995, 16, 385-95.
Hobbs et al., "Structure-based design of peptidomimetic 12 antagonists of p56Ick SH2 domain." Bioorganic & medicinal chemistry letters, May 20, 2002 (May 20, 2002), p. 1365, England, Retrieved from the Internet.
Ibuka et al., "Crystal structure of extended-spectrum beta-lactamase Toho-1: insights into the molecular mechanism for catalytic reaction and substrate specificity expansion." Biochemistry 2003, 42, 10634-43.
Irwin et al., "Zinc—a free database of commercially available compounds for virtual screening." J Chem Int Model. 2005, 45, 177-82.
Jacobs et al., "Cytosolic intermediates for cell wall biosynthesis and degradation control inducible nducible beta-lactam resistance in gram-negative bacteria." Cell 1997, 88, 823-832.
Ke et al., "Novel insights into the mode of inhibition of class A SHV-1 beta-lactamases revealed by boronic acid transition state inhibitors." Antimicrob Agents Chemother 55, 174-83.
Livermore et al., "NXL104 combinations versus Enterobacteriaceae with CTX-M extended-spectrum .beta.-lactamases and carbapenemases." Journal of Antimicrobial Chemotherapy, Oxford University Press, GB, vo 1 .cndot. 62, No. 5, Nov. 1, 2008 (Nov. 1, 2008), pp. 1053-1056.
Livermore,"beta-Lactamases in laboratory and clinical resistance." Clin Microbiol Rev 1995, 8, 557-84.
Lorber et al., "Hierarchical docking of databases of multiple ligand conformations." Curr Top Med Chem. 2005, 5, 739-49.
Makovec et al., "Antiallergic and cytoprotective activity of new N-phenylbenzamido acid derivatives." J Med Chem 1992, 35, 3633-40.
Nichols, et al., Fragment-based inhibitor discovery against B-lactamase; Future Med. Chem (2014) 6(4), 413-427.
Nichols, et al., Structure-Based Design of Potent and Ligand-Efficient Inhibitors of CTX-M Class A B-Lactamase; 2012 American Chemical Society 55, 2163-2172.
Otwinowski et al., "Processing of X-ray diffraction data collected in oscillation mode." Methods in Enzymology 1997, 276, 307-326.
Pages et al., "Efflux pump, the masked side of beta-lactam resistance in Klebsiella pneumoniae clinical isolates." PLoS ONE 2009, 4, e4817.
Payne et al., "Drugs for bad bugs: confronting the challenges of antibacterial discovery." Nat Rev Drug Discov. 2007, 6, 29-40.
Petrosino et al., "T. beta-Lactamases: protein evolution in real time." Trends Microbial 1998, 6, 323-7.
Renslo, "Antibacterial oxazolidinones: emerging structure-toxicity relationships." Expert Rev Anti Infect Ther 2010, 8, 565-74.
Ryckmans et al. "Rapid assessment of a novel series of selective CB2 agonists using parallel synthesis protocols: A Lipophilic Efficiency (LipE) analysis." Bioorganic & Medicinal Chemistry Letters 2009, 19, 4406-4409.
Shimamura et al., "Acyl-intermediate structures of the extended-spectrum class A beta-lactamase, Toho-1, in complex with cefotaxime, cephalothin, and benzylpenicillin." J Biol Chem 2002, 277, 46601-8.
Silvaggi et al., "The crystal structure of phosphonateinhibited D-Ala-D-Ala peptidase reveals an analogue of a tetrahedral transition state." Biochemistry. 2003, 42, 1199-208.

(56) References Cited

OTHER PUBLICATIONS

Sung et al. (CAPLUS Abstract of WO 2008048991) (published Apr. 2008).
Taubes, "The bacteria tight back." Science 2008, 321, 356-61.
Tipper et al., "Mechanism of action of penicillins: a proposal based on their structural similarity to acyl-D-alanyl-D-alanine." Proc Natl Acad Sci U S A 1965, 54, 1133-41.
Tomanicek et al., "Neutron diffraction studies of a class A beta-lactamase Toho-1 E166A/R274N/R276N triple mutant." J Mol Biol 396, 1070-80.
Wang et al., "Evolution of an antibiotic resistance enzyme constrained by stability and activity trade-offs." J Mol Biol 2002, 320, 85-95.
European Search Report for Application No. 13733664.0 dated Apr. 29, 2015 (11 pages).
International Search Report and Written Opinion for Application No. PCT/US2013/020212 dated Apr. 29, 2013 (11 pages).
Japanese Office Action and letter (English Translation) reporting the office action; Application No. 2014-551327 dated Sep. 27, 2016; total pages including translation: 11.
European Patent Office Action for Application No. 13733664.0 dated Oct. 20, 2016 (7 pages).
International Preliminary Report on Patentability for Application No. PCT/US2013/020212 dated Jul. 8, 2014 (7 pages).

\* cited by examiner

Table 1. Analogs designed to target hydrophobic shelf formed by Pro167

| Compound | R = | Ki (μM) | L.E.[a] | LipE[b] |
|---|---|---|---|---|
| 1 | F | 21 | 0.30 | 1.37 |
| 2 | Cl | 6.2 | 0.34 | 1.63 |
| 3 | Me | 4.5 | 0.35 | 1.84 |
| 4 | Br | 3.0 | 0.36 | 1.74 |
| 5 | cyclopropyl | 3.1 | 0.33 | 1.74 |
| 6 | OMe | 17.1 | 0.30 | 1.95 |
| 7 | Ac | 10.2 | 0.30 | 2.51 |
| 8 | $NO_2$ | 3.8 | 0.32 | 2.45 |
| 9 | $CO_2Me$ | 6.9 | 0.29 | 2.09 |
| 10 | $CF_3$ | 2.4 | 0.32 | 1.73 |
| 11 | 2-pyrimidyl | 9.7 | 0.26 | 1.57 |

[a] LE, ligand efficiency; $\Delta G_{bind}$(kcal)/(Number of heavy atoms). [b] LipE = pKi − clogP (clogP calculated using MarvinSketch 5.5.0.1).

Table 2. Analogs designed to target Asp240

| Compound | R = | Ki (μM) | L.E.[a] | LipE[b] |
|---|---|---|---|---|
| 12 | | 76.0 | 0.23 | 2.22 |
| 13 | | no inhibition | N/A | N/A |
| 14 | | 7.2 | 0.32 | 2.27 |
| 15 | | 6.6 | 0.31 | 2.05 |
| 16 | | 1.3 | 0.35 | 3.58 |
| 17 | | 1.9 | 0.34 | 2.59 |
| 18 | | 1.1 | 0.35 | 3.55 |

[a] LE, ligand efficiency; $\Delta G_{bind}$(kcal)/(Number of heavy atoms). [b] LipE = pKi − clogP (clogP calculated using MarvinSketch 5.5.0.1).

Table 3. Analogs designed to target both Pro167 and Asp240

| Compound | R = | Ki (μM) | L.E.[a] | LipE[b] |
|---|---|---|---|---|
| 19 | (benzimidazole-CF₃) | 0.089 | 0.36 | 3.86 |
| 20 | (phenyl-OH, Br) | 0.57 | 0.39 | 2.74 |
| 21 | (phenyl-OH, CF₃) | 0.63 | 0.34 | 2.59 |
| 22 | (phenyl-NH₂, CF₃) | 1.0 | 0.33 | 2.89 |
| 23 | (benzimidazole-F) | 2.7 | 0.32 | 3.11 |
| 24 | (phenyl-CN, Br) | 34.1 | 0.26 | 0.83 |

[a] LE, ligand efficiency; $\Delta G_{bind}$(kcal)/(Number of heavy atoms). [b] LipE = pKi − clogP (clogP calculated using MarvinSketch 5.5.0.1).

Table X-ray Data Collection and Refinement Statistics

Data Collection

| Compound | 4 | 10 | 11 | 12 | 16 | 18 |
|---|---|---|---|---|---|---|
| space group | P2$_1$ | P2$_1$ | P2$_1$ | P2$_1$ | P2$_1$ | P2$_1$ |
| cell dimensions | | | | | | |
| a, b, c (Å) | 45.174 | 45.014 | 45.245 | 45.125 | 45.192 | 45.166 |
| | 107.188 | 107.105 | 106.941 | 106.922 | 106.565 | 106.567 |
| | 47.487 | 47.509 | 47.681 | 47.481 | 47.669 | 47.825 |
| α, β, γ (°) | 90 | 90 | 90 | 90 | 90 | 90 |
| | 100.38 | 102.105 | 100.972 | 101.469 | 101.717 | 101.857 |
| | 90 | 90 | 90 | 90 | 90 | 90 |
| resolution (Å) | 50-1.4 | 50-1.4 | 50-1.4 | 50-1.4 | 50-1.1 | 50-1.3 |
| no. reflections | 75901 | 92455 | 87996 | 86200 | 158174 | 118432 |
| R$_{merge}$ (%) | 6.3 | 6.0 | 5.6 | 7.0 | 5.7 | 4.2 |
| I / σI | 12.9(2.2) | 17.9(2.1) | 18.2(2.1) | 14.8(2.1) | 21.2(4.0) | 14.7(3.0) |
| completeness (%) | 95.0 | 98.9 | 92.5 | 99.7 | 93.3 | 99.4 |
| redundancy | 2.5 | 3.7 | 3.7 | 3.7 | 3.6 | 3.7 |

Refinement

| | | | | | | |
|---|---|---|---|---|---|---|
| resolution (Å) | 50-1.4 | 50-1.4 | 50-1.4 | 50-1.4 | 50-1.1 | 50-1.3 |
| Rwork/Rfree (%) | 15.8/20.1 | 15.5/19.0 | 15.2/19.8 | 15.0/19.4 | 12.8/16.2 | 11.6/16.0 |
| no. heavy atoms | | | | | | |
| protein | 4010 | 3950 | 3972 | 4046 | 4088 | 4024 |
| ligand/ion | 236 | 297 | 80 | 102 | 48 | 79 |
| water | 507 | 600 | 595 | 655 | 754 | 906 |
| B-factors (Å$^2$) | | | | | | |
| protein | 11.83 | 12.80 | 8.986 | 10.56 | 7.118 | 8.975 |
| ligand/ion | 24.02 | 24.33 | 13.60 | 14.07 | 6.971 | 14.79 |
| water | 26.57 | 29.18 | 27.41 | 29.00 | 19.80 | 25.07 |
| rms deviations | | | | | | |
| bond lengths (Å) | 0.013 | 0.013 | 0.0108 | 0.0116 | 0.0168 | 0.0157 |
| bond angles (°) | 1.551 | 1.596 | 1.3896 | 1.347 | 1.7347 | 1.717 |
| ramanchandran plot | | | | | | |
| most favored region | 96.8 | 97.0 | 97.1 | 96.7 | 96.8 | 96.8 |
| additionally allowed | 1.8 | 2.0 | 1.6 | 2.0 | 2.0 | 1.9 |
| generously allowed | 1.4 | 1.0 | 1.2 | 1.3 | 1.1 | 1.3 |

FIG. 7

COMPOSITIONS, METHODS OF USE, AND METHODS OF TREATMENT

CLAIM OF PRIORITY TO RELATED APPLICATION

This application is continuation of US patent application entitled "COMPOSITIONS, METHODS OF USE, AND METHODS OF TREATMENT" having Ser. No. 14/370,715 and filed Jul. 3, 2014, which is the 35 U.S.C. § 371 national stage of, and claims priority to and the benefit of, PCT application PCT/US2013/020212, filed Jan. 4, 2013, where the PCT application claims priority to and the benefit of U.S. Provisional Application No. 61/583,679, filed on Jan. 6, 2012, herein incorporated by reference in its entirety.

BACKGROUND

Beta-lactam compounds such as penicillins are the most widely used antibiotics due to their effective inhibition of the transpeptidases required for bacterial cell wall synthesis. Beta-lactamases catalyze β-lactam hydrolysis and are primary mediators of bacterial resistance to these compounds. There are four β-lactamase families, Classes A to D, among which Classes A and C are the most commonly observed in the clinic. CTX-M is a new group of Class A β-lactamases that is particularly effective against the extended spectrum β-lactam antibiotics such as cefotaxime, which itself was developed to counter bacterial resistance to first-generation penicillins and cephalosporins. The widespread emergence of extended spectrum beta-lactamase (ESBL) such as CTX-M will continue to limit treatment options for bacterial infections. Since its discovery in the 1990s, CTX-M has become the most frequently observed ESBL in many regions of the world.

The use of a β-lactamase inhibitor in combination with a β-lactam antibiotic is a well-established strategy to counter resistance. Existing β-lactamase inhibitors (e.g., clavulanic acid) generally also contain a β-lactam ring, making them susceptible to resistance stemming from up-regulation of β-lactamase production, selection for new β-lactamases, and other mechanisms evolved over millions of years' chemical warfare between bacteria and β-lactam producing microorganisms. Thus, there is a need to address these issues.

SUMMARY

In accordance with the purpose(s) of the present disclosure, as embodied and broadly described herein, embodiments of the present disclosure, in one aspect, relate to a beta-lactamase inhibitor, pharmaceutical compositions including a beta-lactamase inhibitor, methods of treatment of a condition (e.g., infection) or disease, methods of treatment using compositions or pharmaceutical compositions, and the like.

In an embodiment, a composition, among others, includes: a beta-lactamase inhibitor. In an embodiment, the composition also includes an antibiotic such as a beta-lactam antibiotic.

In an embodiment the beta-lactamase inhibitor can be represented by any one of the structures described by structure A:

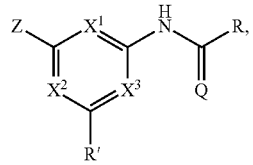

Compound A wherein Z is selected from one of the following moieties:

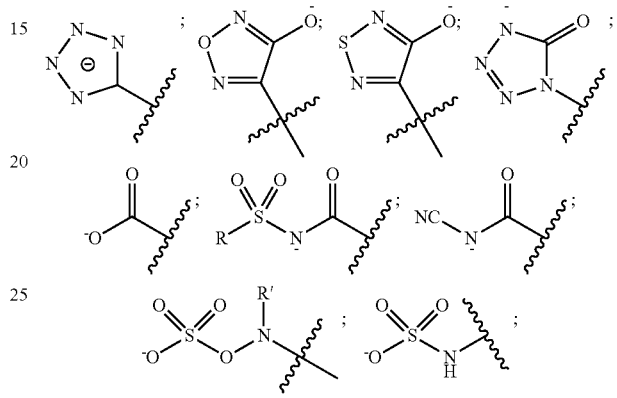

wherein $X^1$, $X^2$, and $X^3$ are each independently selected from C—R' or N; wherein R' is H, a halogen, a substituted or unsubstituted alkyl, a substituted or unsubstituted aryl, a substituted or unsubstituted cycloalkyl, a substituted or unsubstituted cycloalkenyl, a substituted or unsubstituted heteroaryl, a substituted or unsubstituted biaryl, a substituted or unsubstituted fused aryl, a substituted or unsubstituted alkenyl, or a substituted or unsubstituted alkynyl; wherein R is an alkyl group, an aryl group, a heteroaryl group, or a cyclic or heterocyclic group; and Q is O or S.

In an embodiment the beta-lactamase inhibitor can be represented by any one of the structures described by structure B:

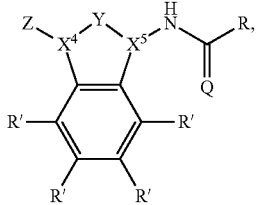

Compound B wherein Z is selected from one of the following:

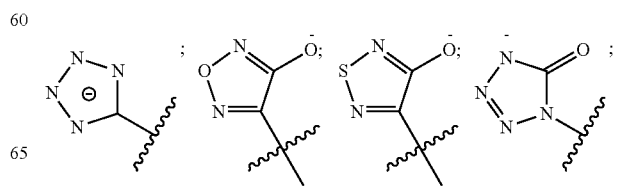

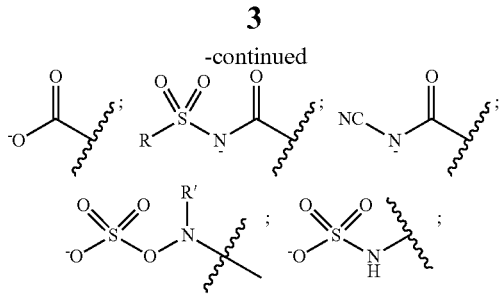

wherein $X^4$ and $X^5$ are each independently selected from CH or N, wherein Y is selected from —CH$_2$—, —CHR'—, —CR'(R')—, >C=O, —S—. —S(=O)—, or —S(=O)$_2$—, wherein R' is H, a halogen, a substituted or unsubstituted alkyl, a substituted or unsubstituted aryl, a substituted or unsubstituted cycloalkyl, a substituted or unsubstituted cycloalkenyl, a substituted or unsubstituted heteroaryl, a substituted or unsubstituted biaryl, a substituted or unsubstituted fused aryl, a substituted or unsubstituted alkenyl, or a substituted or unsubstituted alkynyl, wherein R is an alkyl group, an aryl group, a heteroaryl group, or a cyclic or heterocyclic group; and wherein Q is O or S.

In an embodiment, a pharmaceutical composition, among others, includes: a therapeutically effective amount of a beta-lactamase inhibitor, or a pharmaceutically acceptable salt of the beta-lactamase inhibitor, and a pharmaceutically acceptable carrier, to treat a condition. In an embodiment, the pharmaceutical composition also includes an antibiotic such as a beta-lactam antibiotic. In an embodiment, the beta-lactamase inhibitor can be represented by any one of the structures described by structures A or B as described herein.

In an embodiment, a method of treating a condition, among others, includes: delivering to a subject in need thereof, a pharmaceutical composition, wherein the pharmaceutical composition includes a therapeutically effective amount of a beta-lactamase inhibitor, or a pharmaceutically acceptable salt of the beta-lactamase inhibitor, and a pharmaceutically acceptable carrier, to treat the condition. In an embodiment, the pharmaceutical composition also includes an antibiotic such as a beta-lactam antibiotic. In an embodiment, the beta-lactamase inhibitor can be represented by any one of the structures described by structures A or B as described herein.

Other structures, compositions, methods, features, and advantages will be, or become, apparent to one with skill in the art upon examination of the following drawings and detailed description. It is intended that all such additional structures, systems, methods, features, and advantages be included within this description, be within the scope of the present disclosure, and be protected by the accompanying claims.

BRIEF DESCRIPTION OF THE DRAWINGS

Many aspects of this disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

(FIG. 2A) Compound 4, (FIG. 2B) Compound 10, and (FIG. 2C) Compound 11. The gray dashed lines represent hydrogen bonds between the ligand and CTX-M-9. The carbon atoms of the protein are colored medium gray along with oxygens and nitrogens. Resolution for the structures ranges from 1.2-1.4 Å. Unbiased $2F_o$-$F_c$ densities are shown in blue at 1.5 σ.

(FIG. 3A) Compound 18, (FIG. 3B) Compound 16, and (FIG. 3C) Compound 12, in comparison to the designed pose in cyan. The gray dashed lines represent hydrogen bonds between the ligand and CTX-M-9. Resolution for the structures ranges from 1.2-1.4 Å. Unbiased $2F_o$-$F_c$ densities are shown in blue at 1.5 σ.

FIG. 7 illustrates a table describing the binding of many new inhibitors to the CTX-M active site.

DISCUSSION

Figure 1:
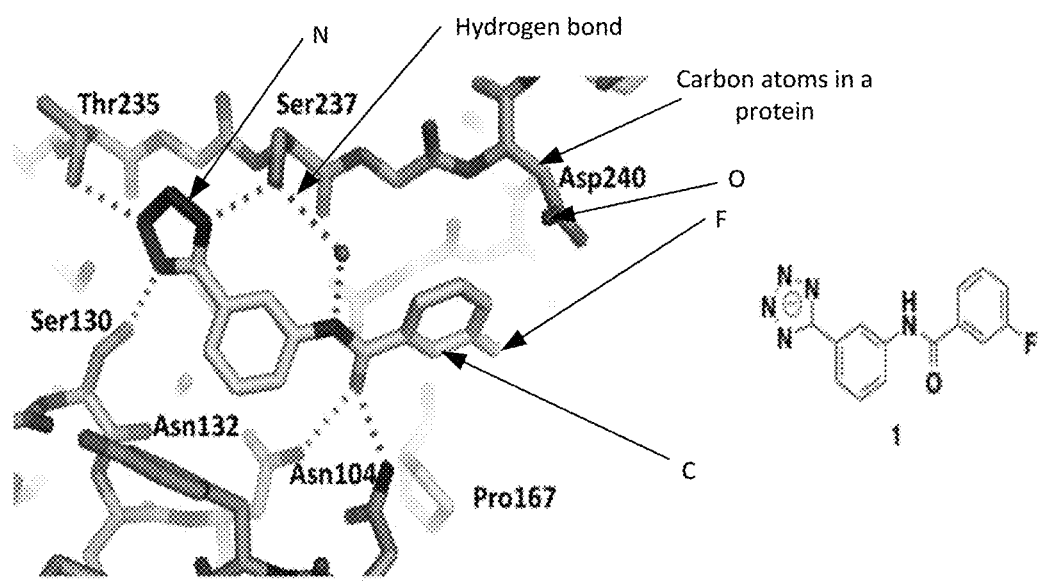
FIG. 1 illustrates the crystal structure of compound 1 in complex with CTX-M-9. Compound 1 (Ki=21 µM) carbon atoms (light gray), nitrogens (dark gray), oxygens (medium gray), and fluorine (very light gray). The dashed lines represent hydrogen bonds with a sphere representing a water molecule.

This disclosure is not limited to particular embodiments described, and as such may, of course, vary. The terminology used herein serves the purpose of describing particular embodiments only, and is not intended to be limiting, since the scope of the present disclosure will be limited only by the appended claims.

Where a range of values is provided, each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method may be carried out in the order of events recited or in any other order that is logically possible.

Embodiments of the present disclosure will employ, unless otherwise indicated, techniques of organic chemistry, biochemistry, molecular biology, pharmacology, medicine, and the like, which are within the skill of the art. Such techniques are explained fully in the literature.

Each of the applications and patents cited in this text, as well as each document or reference cited in each of the applications and patents (including during the prosecution of each issued patent; "application cited documents"), and each of the PCT and foreign applications or patents corresponding to and/or claiming priority from any of these applications and patents, and each of the documents cited or referenced in each of the application cited documents, are hereby expressly incorporated herein by reference. Further, documents or references cited in this text, in a Reference List before the claims, or in the text itself; and each of these documents or references ("herein cited references"), as well as each document or reference cited in each of the herein-cited references (including any manufacturer's specifications, instructions, etc.) are hereby expressly incorporated herein by reference.

Prior to describing the various embodiments, the following definitions are provided and should be used unless otherwise indicated.

Definitions

Unless otherwise defined, all technical and scientific terms used herein have the same meaning as commonly understood by one of ordinary skill in the art of molecular biology, medicinal chemistry, and/or organic chemistry. Although methods and materials similar or equivalent to those described herein can be used in the practice or testing of the present disclosure, suitable methods and materials are described herein.

As used in the specification and the appended claims, the singular forms "a," "an," and "the" may include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

The term "substituted" refers to any one or more hydrogens on the designated atom that can be replaced with a selection from the indicated group, provided that the designated atom's normal valence is not exceeded, and that the substitution results in a stable compound. When a substituent is keto (i.e., C—C(=O)—C), then 2 hydrogens on the atom can be replaced. Keto substituents are not present on aromatic moieties. When a ring system (e.g., carbocyclic or heterocyclic) is substituted with a double bond, it is intended that the carbonyl group or double bond be part of the ring.

The term "aliphatic group" refers to a saturated or unsaturated linear or branched hydrocarbon group and encompasses alkyl, alkenyl, and alkynyl groups, for example.

As used herein, "alkyl" or "alkyl group" refers to a saturated aliphatic hydrocarbon radical which can be straight or branched, having 1 to 20 carbon atoms, wherein the stated range of carbon atoms includes each intervening integer individually, as well as sub-ranges. Examples of alkyl include, but are not limited to methyl, ethyl, n-propyl, i-propyl, n-butyl, s-butyl, t-butyl, n-pentyl, and s-pentyl. The term "lower alkyl" means an alkyl group having less than 10 carbon atoms.

As used herein, "alkenyl" or "alkenyl group" refers to an aliphatic hydrocarbon radical which can be straight or branched, containing at least one carbon-carbon double bond, having 2 to 20 carbon atoms, wherein the stated range of carbon atoms includes each intervening integer individually, as well as sub-ranges. Examples of alkenyl groups include, but are not limited to, ethenyl, propenyl, n-butenyl, i-butenyl, 3-methylbut-2-enyl, n-pentenyl, heptenyl, octenyl, decenyl, and the like.

The term "arylalkyl" refers to an arylalkyl group wherein the aryl and alkyl are as herein described. Examples of arylalkyl include, but are not limited to, -phenylmethyl, -phenylethyl, -phenylpropyl, -phenylbutyl, and -phenylpentyl.

The term "substituted," as in "substituted alkyl", "substituted cycloalkyl," "substituted cycloalkenyl," substituted aryl, "substituted biaryl," "substituted fused aryl" and the like means that the substituted group may contain in place of one or more hydrogens a group such as hydroxy, amino, halo, trifluoromethyl, cyano, —NH(lower alkyl), —N(lower alkyl)$_2$, lower alkoxy, lower alkylthio, or carboxy, and thus embraces the terms haloalkyl, alkoxy, fluorobenzyl, and the sulfur and phosphorous containing substitutions referred to below.

As used herein, "halo", "halogen", or "halogen radical" refers to a fluorine, chlorine, bromine, and iodine, and radicals thereof. Further, when used in compound words, such as "haloalkyl" or "haloalkenyl", "halo" refers to an alkyl or alkenyl radical in which one or more hydrogens are substituted by halogen radicals. Examples of haloalkyl include, but are not limited to, trifluoromethyl, trichloromethyl, pentafluoroethyl, and pentachloroethyl.

The term "alkoxy" represents an alkyl group as defined above with the indicated number of carbon atoms attached through an oxygen bridge. Examples of alkoxy include, but are not limited to, methoxy, ethoxy, n-propoxy, i-propoxy, n-butoxy, s-butoxy, t-butoxy, n-pentoxy, and s-pentoxy. The term "lower alkoxy" means an alkoxy group having less than 10 carbon atoms.

The term "cycloalkyl" refers to a non-aromatic mono- or multicyclic ring system of about 3 to about 10 carbon atoms, preferably of about 5 to about 10 carbon atoms. Preferred ring sizes of rings of the ring system include about 5 to about 6 ring atoms. Exemplary monocyclic cycloalkyl include cyclopentyl, cyclohexyl, cycloheptyl, and the like. Exemplary multicyclic cycloalkyl include 1-decalin, norbornyl, adamant-(1- or 2-)yl, and the like.

The term "cycloalkenyl" refers to a non-aromatic mono- or multicyclic ring system of about 3 to about 10 carbon atoms, preferably of about 5 to about 10 carbon atoms, and which contains at least one carbon-carbon double bond. Preferred ring sizes of rings of the ring system include about 5 to about 6 ring atoms. Exemplary monocyclic cycloalkenyl include cyclopentenyl, cyclohexenyl, cycloheptenyl, and the like. An exemplary multicyclic cycloalkenyl is norbornylenyl.

The term "aryl" as used herein, refers to an aromatic monocyclic or multicyclic ring system of about 6 to about 14 carbon atoms, preferably of about 6 to about 10 carbon atoms. Exemplary aryl groups include phenyl or naphthyl, or phenyl substituted or naphthyl substituted.

The term "heteroaryl" is used herein to denote an aromatic ring or fused ring structure of carbon atoms with one or more non-carbon atoms, such as oxygen, nitrogen, and sulfur, in the ring or in one or more of the rings in fused ring structures. Examples are furanyl, pyranyl, thienyl, imidazyl, pyrrolyl, pyridyl, pyrazolyl, pyrazinyl, pyrimidinyl, indolyl, indazolyl, quinolyl, isoquinolyl, quinoxalyl, and quinazolinyl. Preferred examples are furanyl, indazolyl, imidazyl, pyranyl, pyrrolyl, and pyridyl.

The term "biaryl" refers to an aryl, as defined above, where two aryl groups are joined by a direct bond or through an intervening alkyl group, preferably a lower alkyl group.

The term "fused aryl" refers to a multicyclic ring system as included in the term "aryl," and includes aryl groups and heteroaryl groups that are condensed. Examples are naphthyl, anthryl and phenanthryl. The bonds can be attached to any of the rings.

"Aralkyl" and "heteroaralkyl" refer to aryl and heteroaryl moieties, respectively, that are linked to a main structure by an intervening alkyl group, e.g., containing one or more methylene groups.

The term "fluorobenzyl" refers to a benzyl group wherein the phenyl moiety is substituted with one or more fluorine atoms, including 2, 3, 4 and 5 fluorine atom substituents.

Similarly, "halobenzyl" refers to benzyl substituted with one or more different halogens, including fluorine, chlorine, bromine, and iodine (not astatine).

The terms "sulfide" and "thioether" as used herein, alone or in combination, refer to a sulfur atom covalently linked to two atoms; the formal oxidation state of said sulfur is (II). These terms may be used interchangeably.

The term "sulfanyl" as used herein, alone or in combination, refers to the —S—R group, wherein R may be a group such as: alkyl, alkenyl, alkynyl, aryl, alicyclic, heterocyclic, aryl, heteroaryl, arylalkyl and heteroarylalkyl, wherein the alkyl, alkenyl, alkynyl, aryl, alicyclic, heterocyclic, aryl, heteroaryl, arylalkyl and heteroarylalkyl groups may be optionally substituted. Non-limiting examples of sulfanyl groups include methylsulfanyl (—$SCH_3$) and iso-propylsulfanyl (—$SCH(CH_3)_2$) and the like.

The term "sulfoxide" as used herein, alone or in combination, refers to a sulfur atom covalently linked to three atoms, at least one of which is an oxygen atom; the formal oxidation state of said sulfur atom is (IV).

The term "sulfinyl" as used herein, alone or in combination, refers to the groups —S(O)—R, wherein R may be, but is not limited to alkyl, alkenyl, alkynyl, aryl, alicyclic, heterocyclic, aryl, heteroaryl, arylalkyl and heteroarylalkyl, wherein the alkyl, alkenyl, alkynyl, aryl, alicyclic, heterocyclic, aryl, heteroaryl, arylalkyl and heteroarylalkyl groups may be optionally substituted. A non-limiting example of a sulfinyl group includes methylsulfinyl (—$S(O)CH_3$) and the like.

The term "sulfone" as used herein, alone or in combination, refers to a sulfur atom covalently linked to four atoms, at least two of which are oxygen atoms; the formal oxidation state of said sulfur atom is (VI).

The term "sulfonyl" as used herein, alone or in combination, refers to the groups —$S(O_2)$—R, wherein R may be, but is not limited to, alkyl, alkenyl, alkynyl, aryl, alicyclic, heterocyclic, aryl, heteroaryl, arylalkyl and heteroarylalkyl, wherein the alkyl, alkenyl, alkynyl, aryl, alicyclic, heterocyclic, aryl, heteroaryl, arylalkyl and heteroarylalkyl groups may be optionally substituted. A non-limiting example of a sulfonyl group includes methylsulfonyl (—$S(O_2)CH_3$) and the like.

The term "phosphite" as used herein, alone or in combination, refers to a phosphorus atom covalently linked to three carbon atoms, wherein the formal oxidation state of said phosphorus is (III).

The term "phosphinyl" as used herein, alone or in combination, refers to the monoradical derived from a phosphite group, as defined above.

The term "phosphonate" as used herein, alone or in combination, refers to a phosphorus atom covalently linked to four atoms, three of which are oxygen and one of which is carbon wherein the formal oxidation state of said phosphorus is (V).

The term "phosphonyl" as used herein, alone or in combination, refers to the monoradical derived from a phosphonate group, as defined above.

The term "phosphate" as used herein, alone or in combination, refers to a phosphorus atom covalently linked to four oxygen atoms, wherein the formal oxidation state of said phosphorus is (V).

The term "phosphatidyl" as used herein, alone or in combination, refers to the monoradical derived from a phosphate group, as defined above.

The terms ketone, ester, ether, and acyl have their art recognized meanings.

The term "unit dosage form," as used herein, refers to physically discrete units suitable as unitary dosages for human and/or animal subjects, each unit containing a predetermined quantity of a compound (e.g., compositions or pharmaceutical compositions, as described herein) calculated in an amount sufficient to produce the desired effect in association with a pharmaceutically acceptable diluent, carrier or vehicle. The specifications for unit dosage forms depend on the particular compound employed, the route and frequency of administration, and the effect to be achieved, and the pharmacodynamics associated with each compound in the host.

A "pharmaceutically acceptable excipient," "pharmaceutically acceptable diluent," "pharmaceutically acceptable carrier," or "pharmaceutically acceptable adjuvant" means an excipient, diluent, carrier, and/or adjuvant that are useful in preparing a pharmaceutical composition that are generally safe, non-toxic and neither biologically nor otherwise undesirable, and include an excipient, diluent, carrier, and adjuvant that are acceptable for veterinary use and/or human pharmaceutical use. "A pharmaceutically acceptable excipient, diluent, carrier and/or adjuvant" as used in the specification and claims includes one and more such excipients, diluents, carriers, and adjuvants.

As used herein, a "pharmaceutical composition" is meant to encompass a composition or pharmaceutical composition suitable for administration to a subject, such as a mammal, especially a human. In general a "pharmaceutical composition" is sterile, and preferably free of contaminants that are capable of eliciting an undesirable response within the subject (e.g., the compound(s) in the pharmaceutical composition is pharmaceutical grade). Pharmaceutical compositions can be designed for administration to subjects or patients in need thereof via a number of different routes of administration including oral, intravenous, buccal, rectal, parenteral, intraperitoneal, intradermal, intracheal, intramuscular, subcutaneous, inhalational and the like.

The term "therapeutically effective amount" as used herein refers to that amount of an embodiment of the composition or pharmaceutical composition being administered that will relieve to some extent one or more of the symptoms of the disease, i.e., infection, being treated, and/or that amount that will prevent, to some extent, one or more of the symptoms of the disease, i.e., infection, that the host being treated has or is at risk of developing.

"Pharmaceutically acceptable salt" refers to those salts that retain the biological effectiveness and optionally other properties of the free bases and that are obtained by reaction with inorganic or organic acids such as hydrochloric acid, hydrobromic acid, sulfuric acid, nitric acid, phosphoric acid, methanesulfonic acid, ethanesulfonic acid, p-toluenesulfonic acid, salicylic acid, malic acid, maleic acid, succinic acid, tartaric acid, citric acid, and the like.

In the event that embodiments of the disclosed compounds in the composition or pharmaceutical composition form salts, these salts are within the scope of the present disclosure. Reference to a compound used in the composition or pharmaceutical composition of any of the formulas herein is understood to include reference to salts thereof, unless otherwise indicated. The term "salt(s)", as employed herein, denotes acidic and/or basic salts formed with inorganic and/or organic acids and bases. In addition, when a compound contains both a basic moiety and an acidic moiety, zwitterions ("inner salts") may be formed and are included within the term "salt(s)" as used herein. Pharmaceutically acceptable (e.g., non-toxic, physiologically acceptable) salts are preferred, although other salts are also useful, e.g., in isolation or purification steps which may be employed during preparation. Salts of the compounds of a compound may be formed, for example, by reacting the compound with an amount of acid or base, such as an equivalent amount, in a medium such as one in which the salt precipitates or in an aqueous medium followed by lyophilization.

Embodiments of the compounds of the composition or pharmaceutical composition of the present disclosure that contain a basic moiety may form salts with a variety of organic and inorganic acids. Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecyl sulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, 2-hydroxyethanesulfonates, lactates, maleates (formed with maleic acid), methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

Embodiments of the compounds of the composition or pharmaceutical composition of the present disclosure that contain an acidic moiety may form salts with a variety of organic and inorganic bases. Exemplary basic salts include ammonium salts, alkali metal salts such as sodium, lithium, and potassium salts, alkaline earth metal salts such as calcium and magnesium salts, salts with organic bases (for example, organic amines) such as benzathines, dicyclohexylamines, hydrabamines (formed with N,N-bis(dehydroabietyl)ethylenediamine), N-methyl-D-glucamines, N-methyl-D-glucamides, t-butyl amines, and salts with amino acids such as arginine, lysine, and the like.

Basic nitrogen-containing groups may be quaternized with agents such as lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl and stearyl chlorides, bromides and iodides), aralkyl halides (e.g., benzyl and phenethyl bromides), and others.

Solvates of the compounds of the composition or pharmaceutical composition of the present disclosure are also contemplated herein.

To the extent that the disclosed the compounds of the composition or pharmaceutical composition of the present disclosure, and salts thereof, may exist in their tautomeric form, all such tautomeric forms are contemplated herein as part of the present disclosure.

All stereoisomers of the compounds of the composition or pharmaceutical composition of the present disclosure, such as those that may exist due to asymmetric carbons on the various substituents, including enantiomeric forms (which may exist even in the absence of asymmetric carbons) and diastereomeric forms are contemplated within the scope of this disclosure. Individual stereoisomers of the compounds of the disclosure may, for example, be substantially free of other isomers, or may be admixed, for example, as racemates or with all other, or other selected, stereoisomers. The stereogenic centers of the compounds of the present disclosure can have the S or R configuration as defined by the IUPAC 1974 Recommendations.

The term "prodrug" refers to an inactive precursor of the compounds of the composition or pharmaceutical composition of the present disclosure that is converted into a biologically active form in vivo. Prodrugs are often useful because, in some situations, they may be easier to administer than the parent compound. They may, for instance, be bioavailable by oral administration whereas the parent compound is not. The prodrug may also have improved solubility in pharmaceutical compositions over the parent drug. A prodrug may be converted into the parent drug by various mechanisms, including enzymatic processes and metabolic hydrolysis. Harper, N.J. (1962). Drug Latentiation in Jucker, ed. Progress in Drug Research, 4:221-294; Morozowich et al. (1977). Application of Physical Organic Principles to Prodrug Design in E. B. Roche ed. Design of Biopharmaceutical Properties through Prodrugs and Analogs, APhA; Acad. Pharm. Sci.; E. B. Roche, ed. (1977). Bioreversible Carriers in Drug in Drug Design, Theory and Application, APhA; H. Bundgaard, ed. (1985) Design of Prodrugs, Elsevier; Wang et al. (1999) Prodrug approaches to the improved delivery of peptide drug, Curr. Pharm. Design. 5(4):265-287; Pauletti et al. (1997). Improvement in peptide bioavailability: Peptidomimetics and Prodrug Strategies, Adv. Drug. Delivery Rev. 27:235-256; Mizen et al. (1998). The Use of Esters as Prodrugs for Oral Delivery of β-Lactam antibiotics, Pharm. Biotech. 11:345-365; Gaignault et al. (1996). Designing Prodrugs and Bioprecursors I. Carrier Prodrugs, Pract. Med. Chem. 671-696; M. Asgharnej ad (2000). Improving Oral Drug Transport Via Prodrugs, in G. L. Amidon, P. I. Lee and E. M. Topp, Eds., Transport Processes in Pharmaceutical Systems, Marcell Dekker, p. 185-218; Balant et al. (1990) Prodrugs for the improvement of drug absorption via different routes of administration, Eur. J. Drug Metab. Pharmacokinet., 15(2): 143-53; Balimane and Sinko (1999). Involvement of multiple transporters in the oral absorption of nucleoside analogues, Adv. Drug Delivery Rev., 39(1-3):183-209; Browne (1997). Fosphenytoin (Cerebyx), Clin. Neuropharmacol. 20(1): 1-12; Bundgaard (1979). Bioreversible derivatization of drugs—principle and applicability to improve the therapeutic effects of drugs, Arch. Pharm. Chemi. 86(1): 1-39; H. Bundgaard, ed. (1985) Design of Prodrugs, New York: Elsevier; Fleisher et al. (1996). Improved oral drug delivery: solubility limitations overcome by the use of prodrugs, Adv. Drug Delivery Rev. 19(2): 115-130; Fleisher et al. (1985). Design of prodrugs for improved gastrointestinal absorption by intestinal enzyme targeting, Methods Enzymol. 112: 360-81; Farquhar D, et al. (1983). Biologically Reversible Phosphate-Protective Groups, J. Pharm. Sci., 72(3): 324-325; Han, H. K. et al. (2000). Targeted prodrug design to optimize drug delivery, AAPS PharmSci., 2(1): E6; Sadzuka Y. (2000). Effective prodrug liposome and conversion to active metabolite, Curr. Drug Metab., 1(1):31-48; D. M. Lambert (2000) Rationale and applications of lipids as prodrug carriers, Eur. J. Pharm. Sci., 11 Suppl 2:S15-27; Wang, W.

et al. (1999) Prodrug approaches to the improved delivery of peptide drugs. Curr. Pharm. Des., 5(4):265-87.

The term "administration" refers to introducing a composition of the present disclosure into a host. One preferred route of administration of the composition is oral administration. Another preferred route is intravenous administration. However, any route of administration, such as topical, subcutaneous, peritoneal, intraarterial, inhalation, vaginal, rectal, nasal, introduction into the cerebrospinal fluid, or instillation into body compartments can be used.

As used herein, "treat", "treatment", "treating", and the like refer to acting upon a condition, a disease or a disorder with a composition to affect the condition, disease or disorder by improving or altering it. The improvement or alteration may include an improvement in symptoms or an alteration in the physiologic pathways associated with the condition, disease, or disorder. "Treatment," as used herein, covers one or more treatments of a tumor or a disease in a host (e.g., a mammal, typically a human or non-human animal of veterinary interest), and includes: (a) reducing the risk of occurrence of the disease in a subject determined to be predisposed to the condition or disease but not yet diagnosed with it (b) impeding the development of the condition or disease, and/or (c) relieving the condition disease, e.g., causing regression of the condition or disease and/or relieving one or more disease symptoms.

As used herein, the terms "prophylactically treat" or "prophylactically treating" refers completely or partially preventing (e.g., about 50% or more, about 60% or more, about 70% or more, about 80% or more, about 90% or more, about 95% or more, or about 99% or more) a condition, a disease, or a symptom thereof and/or may be therapeutic in terms of a partial or complete cure for a condition, a disease, and/or adverse effect attributable to the disease.

As used herein, the term "host," "subject," or "patient," includes humans and mammals (e.g., mice, rats, pigs, cats, dogs, and horses). Typical hosts to which compounds of the present disclosure may be administered will be mammals, particularly primates, especially humans. For veterinary applications, a wide variety of subjects will be suitable, e.g., livestock such as cattle, sheep, goats, cows, swine, and the like; poultry such as chickens, ducks, geese, turkeys, and the like; and domesticated animals particularly pets such as dogs and cats. For diagnostic or research applications, a wide variety of mammals will be suitable subjects, including rodents (e.g., mice, rats, hamsters), rabbits, primates, and swine such as inbred pigs and the like. The term "living host" refers to a host noted above or another organism that is alive. The term "living host" refers to the entire host or organism and not just a part excised (e.g., a liver or other organ) from the living host.

Discussion

The present disclosure provides compositions including a beta-lactamase inhibitor, pharmaceutical compositions including a beta-lactamase inhibitor, methods of treatment of a condition (e.g., infection) or disease, methods of treatment using compositions or pharmaceutical compositions, and the like. An embodiment of the present disclosure can be used in combination (e.g., in the same composition or separately) to treat resistant strains of bacteria (e.g., MRSA). Additional details are described in the Examples.

As described in more detail in the Example, CTX-M beta-lactamases are the main resistance mechanisms against extended spectrum beta-lactam antibiotics in many regions of the world. Inhibitors against these proteins can restore the efficacy of beta-lactam antibiotics against resistant bacteria such as MRSA (superbug). Embodiments of the present disclosure describe novel inhibitors against CTX-M beta-lactamases.

In addition, embodiments of the present disclosure include beta-lactamase inhibitors that can be used in combination with a beta-lactam antibiotic to treat resistant strands of bacteria. In an embodiment, the beta-lactam antibiotic can include penicillin and penicillin derivatives, cephalosporin and cephalosporin derivatives, monobactam and monobactam derivatives, carbapenem and carbapenem derivatives, and a combination thereof. In an embodiment, the derivatives described regarding a beta-lactam antibiotic derivatives are those known in the art.

An embodiment of the present disclosure includes a composition and pharmaceutical composition including a beta-lactamase inhibitor. In an embodiment, the pharmaceutical composition and the method of treatment (e.g., of an infection such as one directly or indirectly caused by a bacterial infection) includes a therapeutically effective amount of a beta-lactamase inhibitor, or a pharmaceutically acceptable salt of the beta-lactamase inhibitor, and a pharmaceutically acceptable carrier, to treat a condition (e.g., bacterial infection).

In an embodiment the bacterial infections can be caused by one or more types of bacteria, in particular, drug or multidrug resistant bacteria. In an embodiment, the bacteria can include, but is not limited to, *Staphylococcus aureus, Streptococcus pyogenes, Streptococcus pneumonia, Enterococcus faecalis, Enterococcus faecium, Pseudomonas aeruginosa, Clostridium difficile, Escherichia coli, Salmonella, Acinetobacter baumannii, Mycobacterium tuberculosis*, or a combination thereof.

In an embodiment, the beta-lactamase inhibitor can include structures A, A', A", and A'" as shown below.

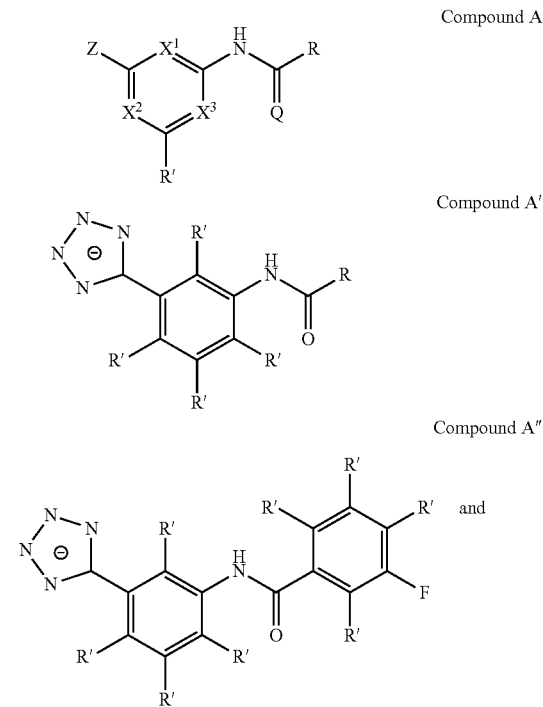

Compound A

Compound A'

Compound A"

and

-continued

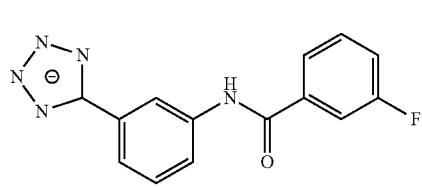

Compound A'''

In an embodiment, Z can be selected from one of the following structures:

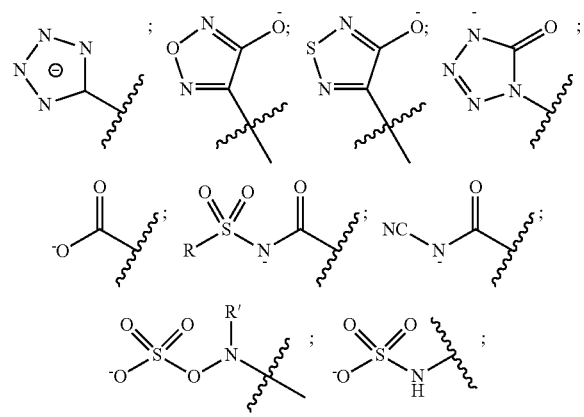

In an embodiment, $X^1$, $X^2$, and $X^3$ can each be independently selected from C—R' or N. Optionally in an embodiment, $X^2$ or $X^3$ can be a bond between the adjacent carbons. In an embodiment, R' can be H, a halogen, a substituted or unsubstituted alkyl, a substituted or unsubstituted aryl, a substituted or unsubstituted cycloalkyl, a substituted or unsubstituted cycloalkenyl, a substituted or unsubstituted heteroaryl, a substituted or unsubstituted biaryl, a substituted or unsubstituted fused aryl, a substituted or unsubstituted alkenyl, or a substituted or unsubstituted alkynyl.

In an embodiment, R can be an alkyl group (e.g., C1 to C5 hydrocarbons such as methyl, ethyl, and the like), an aryl group, a heteroaryl group, or a cyclic or hetero (e.g., 0, N) cyclic group (e.g., C1 to C7 cyclic hydrocarbons). In an embodiment, the R groups described herein can be substituted or unsubstituted.

In an embodiment, Q can be O or S.

In an embodiment, the beta-lactamase inhibitor can include structures:

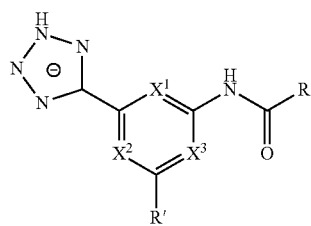

where $X^1$, $X^2$, $X^3$, R, and R' can be described herein in reference to structure A;

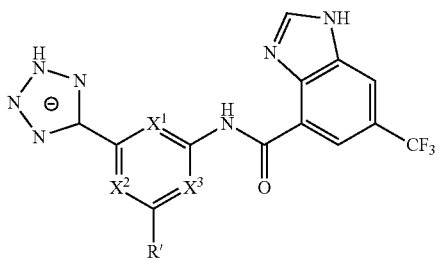

where $X^1$, $X^2$, $X^3$, and R' can be described herein in reference to structure A; and

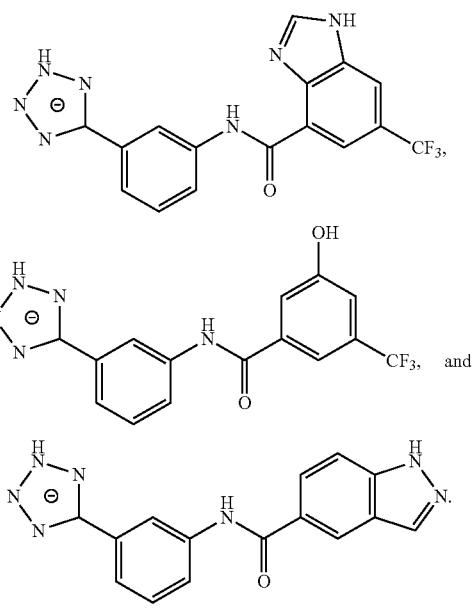

and

In an embodiment, the beta-lactamase inhibitor can include structure B, as shown below.

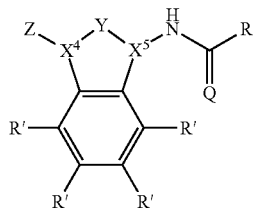

Compound B

In an embodiment, Z can be selected from one of the following:

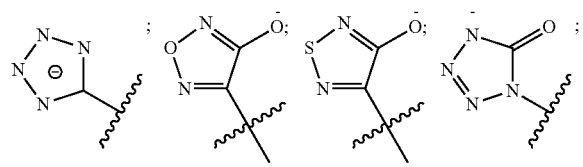

-continued

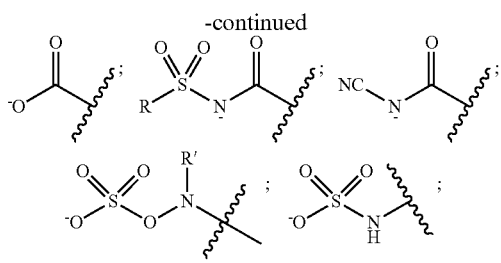

In an embodiment, $X^4$ and $X^5$ can each be independently selected from CH or N.

In an embodiment, Y can be selected from —CH$_2$—, —CHR'—, —CR'(R')—, >C=O, —S—, —S(=O)—, and —S(=O)$_2$—. Optionally in an embodiment, group Y can be absent, in which case $X^4$ and $X^5$ can each be independently selected from CH$_2$ or NH.

In an embodiment, R' can be H, a halogen, a substituted or unsubstituted alkyl, a substituted or unsubstituted aryl, a substituted or unsubstituted cycloalkyl, a substituted or unsubstituted cycloalkenyl, a substituted or unsubstituted heteroaryl, a substituted or unsubstituted biaryl, a substituted or unsubstituted fused aryl, a substituted or unsubstituted alkenyl, or a substituted or unsubstituted alkynyl.

In an embodiment, R can be an alkyl group (e.g., C1 to C5 hydrocarbons such as methyl, ethyl, and the like), an aryl group, a heteroaryl group, or a cyclic or hetero (e.g., O, N) cyclic group (e.g., C1 to C7 cyclic hydrocarbons). In an embodiment, the R groups described herein can be substituted or unsubstituted.

In an embodiment, Q can be O or S.

In an embodiment, the beta-lactamase inhibitor can include structures:

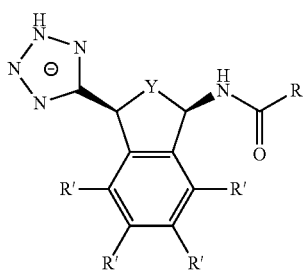

where Y, R, and R' are as described herein reference to structure B; and

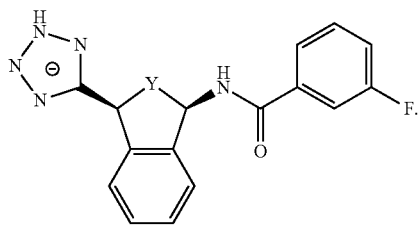

Figure 4:
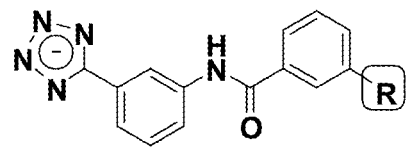
FIG. 4, Table 1, illustrates analogs designed to target hydrophobic shelf formed by Pro167.
Figure 5:
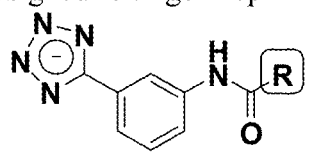
FIG. 5, Table 2, illustrates analogs designed to target Asp240.
Figure 6:
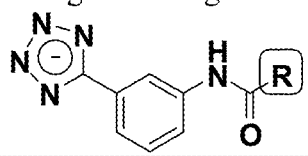
FIG. 6, Table 3, illustrates analogs designed to target both Pro167 and Asp240.

In addition, the R' group in any of the structures listed above can include the structures listed in Tables 1-3 (FIGS. 4-6, respectively) in Example 1.

In an embodiment, the compounds covered by compound A exclude compound A''' for the composition and pharmaceutical compositions. In an embodiment, methods include the compounds covered by compound A including compound A'''. In an embodiment, methods include the compounds covered by compound A excluding compound A'''.

It should be noted that the therapeutically effective amount to result in uptake of the beta-lactamase inhibitor and/or antibiotic (e.g., each either alone or in combination with one another) into the host will depend upon a variety of factors, including for example, the age, body weight, general health, sex, and diet of the host; the time of administration; the route of administration; the rate of excretion of the specific compound employed; the duration of the treatment; the existence of other drugs used in combination or coincidental with the specific composition employed; and like factors well known in the medical arts.

Pharmaceutical Formulations and Routes of Administration

Embodiments of the present disclosure include a beta-lactamase inhibitor as identified herein and can be formulated with one or more pharmaceutically acceptable excipients, diluents, carriers and/or adjuvants. In addition, embodiments of the present disclosure include a beta-lactamase inhibitor formulated with one or more pharmaceutically acceptable auxiliary substances. In particular beta-lactamase inhibitor can be formulated with one or more pharmaceutically acceptable excipients, diluents, carriers, and/or adjuvants to provide an embodiment of a composition of the present disclosure.

A wide variety of pharmaceutically acceptable excipients are known in the art. Pharmaceutically acceptable excipients have been amply described in a variety of publications, including, for example, A. Gennaro (2000) "Remington: The Science and Practice of Pharmacy," 20th edition, Lippincott, Williams, & Wilkins; Pharmaceutical Dosage Forms and Drug Delivery Systems (1999) H. C. Ansel et al., eds. 7th ed., Lippincott, Williams, & Wilkins; and Handbook of Pharmaceutical Excipients (2000) A. H. Kibbe et al., eds., 3rd ed. Amer. Pharmaceutical Assoc.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

In an embodiment of the present disclosure, the beta-lactamase inhibitor can be administered to the host using any means capable of resulting in the desired effect. Thus, the beta-lactamase inhibitor can be incorporated into a variety of formulations for therapeutic administration. For example, the beta-lactamase inhibitor can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants and aerosols.

In pharmaceutical dosage forms, the beta-lactamase inhibitor may be administered in the form of its pharmaceutically acceptable salts, or a subject active composition may be used alone or in appropriate association, as well as in combination, with other pharmaceutically active compounds. The following methods and excipients are merely exemplary and are in no way limiting.

For oral preparations, the beta-lactamase inhibitor can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

Embodiments of the beta-lactamase inhibitor can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

Embodiments of the beta-lactamase inhibitor can be utilized in aerosol formulation to be administered via inhalation. Embodiments of the beta-lactamase inhibitor can be formulated into pressurized acceptable propellants such as dichlorodifluoromethane, propane, nitrogen and the like.

Furthermore, embodiments of the beta-lactamase inhibitor can be made into suppositories by mixing with a variety of bases such as emulsifying bases or water-soluble bases. Embodiments of the beta-lactamase inhibitor can be administered rectally via a suppository. The suppository can include vehicles such as cocoa butter, carbowaxes and polyethylene glycols, which melt at body temperature, yet are solidified at room temperature.

Unit dosage forms for oral or rectal administration, such as syrups, elixirs, and suspensions, may be provided wherein each dosage unit, for example, teaspoonful, tablespoonful, tablet or suppository, contains a predetermined amount of the composition containing one or more compositions. Similarly, unit dosage forms for injection or intravenous administration may comprise the beta-lactamase inhibitor in a composition as a solution in sterile water, normal saline or another pharmaceutically acceptable carrier.

Embodiments of the beta-lactamase inhibitor can be formulated in an injectable composition in accordance with the disclosure. Typically, injectable compositions are prepared as liquid solutions or suspensions; solid forms suitable for solution in, or suspension in, liquid vehicles prior to injection may also be prepared. The preparation may also be emulsified or the active ingredient (triamino-pyridine derivative and/or the labeled triamino-pyridine derivative) encapsulated in liposome vehicles in accordance with the present disclosure.

In an embodiment, the beta-lactamase inhibitor can be formulated for delivery by a continuous delivery system. The term "continuous delivery system" is used interchangeably herein with "controlled delivery system" and encompasses continuous (e.g., controlled) delivery devices (e.g., pumps) in combination with catheters, injection devices, and the like, a wide variety of which are known in the art.

Mechanical or electromechanical infusion pumps can also be suitable for use with the present disclosure. Examples of such devices include those described in, for example, U.S. Pat. Nos. 4,692,147; 4,360,019; 4,487,603; 4,360,019; 4,725,852; 5,820,589; 5,643,207; 6,198,966; and the like. In general, delivery of the beta-lactamase inhibitor can be accomplished using any of a variety of refillable, pump systems. Pumps provide consistent, controlled release over time. In some embodiments, the beta-lactamase inhibitor can be in a liquid formulation in a drug-impermeable reservoir, and is delivered in a continuous fashion to the individual.

In one embodiment, the drug delivery system is an at least partially implantable device. The implantable device can be implanted at any suitable implantation site using methods and devices well known in the art. An implantation site is a site within the body of a subject at which a drug delivery device is introduced and positioned. Implantation sites include, but are not necessarily limited to, a subdermal, subcutaneous, intramuscular, or other suitable site within a subject's body. Subcutaneous implantation sites are used in some embodiments because of convenience in implantation and removal of the drug delivery device.

Drug release devices suitable for use in the disclosure may be based on any of a variety of modes of operation. For example, the drug release device can be based upon a diffusive system, a convective system, or an erodible system (e.g., an erosion-based system). For example, the drug release device can be an electrochemical pump, osmotic pump, an electroosmotic pump, a vapor pressure pump, or osmotic bursting matrix, e.g., where the drug is incorporated into a polymer and the polymer provides for release of drug formulation concomitant with degradation of a drug-impregnated polymeric material (e.g., a biodegradable, drug-impregnated polymeric material). In other embodiments, the drug release device is based upon an electrodiffusion system, an electrolytic pump, an effervescent pump, a piezoelectric pump, a hydrolytic system, etc.

Drug release devices based upon a mechanical or electromechanical infusion pump can also be suitable for use with the present disclosure. Examples of such devices include those described in, for example, U.S. Pat. Nos. 4,692,147; 4,360,019; 4,487,603; 4,360,019; 4,725,852, and the like. In general, a subject treatment method can be accomplished using any of a variety of refillable, non-exchangeable pump systems. Pumps and other convective systems are generally preferred due to their generally more consistent, controlled release over time. Osmotic pumps are used in some embodiments due to their combined advantages of more consistent controlled release and relatively small size (see, e.g., PCT published application no. WO 97/27840 and U.S. Pat. Nos. 5,985,305 and 5,728,396). Exemplary osmotically-driven devices suitable for use in the disclosure include, but are not necessarily limited to, those described in U.S. Pat. Nos. 3,760,984; 3,845,770; 3,916,899; 3,923,426; 3,987,790; 3,995,631; 3,916,899; 4,016,880; 4,036,228; 4,111,202; 4,111,203; 4,203,440; 4,203,442; 4,210,139; 4,327,725; 4,627,850; 4,865,845; 5,057,318; 5,059,423; 5,112,614; 5,137,727; 5,234,692; 5,234,693; 5,728,396; and the like.

In some embodiments, the drug delivery device is an implantable device. The drug delivery device can be implanted at any suitable implantation site using methods and devices well known in the art. As noted herein, an implantation site is a site within the body of a subject at which a drug delivery device is introduced and positioned. Implantation sites include, but are not necessarily limited to a subdermal, subcutaneous, intramuscular, or other suitable site within a subject's body.

In some embodiments, an active agent (e.g., the beta-lactamase inhibitor) can be delivered using an implantable drug delivery system, e.g., a system that is programmable to provide for administration of the agent. Exemplary programmable, implantable systems include implantable infusion pumps. Exemplary implantable infusion pumps, or devices useful in connection with such pumps, are described in, for example, U.S. Pat. Nos. 4,350,155; 5,443,450; 5,814,019; 5,976,109; 6,017,328; 6,171,276; 6,241,704; 6,464,687; 6,475,180; and 6,512,954. A further exemplary device that can be adapted for the present disclosure is the Synchromed infusion pump (Medtronic).

Suitable excipient vehicles for the beta-lactamase inhibitor are, for example, water, saline, dextrose, glycerol, ethanol, or the like, and combinations thereof. In addition, if desired, the vehicle may contain minor amounts of auxiliary substances such as wetting or emulsifying agents or pH buffering agents. Methods of preparing such dosage forms are known, or will be apparent upon consideration of this disclosure, to those skilled in the art. See, e.g., Remington's Pharmaceutical Sciences, Mack Publishing Company, Easton, Pa., 17th edition, 1985. The composition or formulation to be administered will, in any event, contain a quantity of the beta-lactamase inhibitor adequate to achieve the desired state in the subject being treated.

Compositions of the present disclosure can include those that comprise a sustained-release or controlled release matrix. In addition, embodiments of the present disclosure can be used in conjunction with other treatments that use sustained-release formulations. As used herein, a sustained-release matrix is a matrix made of materials, usually polymers, which are degradable by enzymatic or acid-based hydrolysis or by dissolution. Once inserted into the body, the matrix is acted upon by enzymes and body fluids. A sustained-release matrix desirably is chosen from biocompatible materials such as liposomes, polylactides (polylactic acid), polyglycolide (polymer of glycolic acid), polylactide co-glycolide (copolymers of lactic acid and glycolic acid), polyanhydrides, poly(ortho)esters, polypeptides, hyaluronic acid, collagen, chondroitin sulfate, carboxcylic acids, fatty acids, phospholipids, polysaccharides, nucleic acids, polyamino acids, amino acids such as phenylalanine, tyrosine, isoleucine, polynucleotides, polyvinyl propylene, polyvinylpyrrolidone and silicone. Illustrative biodegradable matrices include a polylactide matrix, a polyglycolide matrix, and a polylactide co-glycolide (co-polymers of lactic acid and glycolic acid) matrix.

In another embodiment, the pharmaceutical composition of the present disclosure (as well as combination compositions) can be delivered in a controlled release system. For example, the beta-lactamase inhibitor may be administered using intravenous infusion, an implantable osmotic pump, a transdermal patch, liposomes, or other modes of administration. In one embodiment, a pump may be used (Sefton (1987). *CRC Crit. Ref. Biomed. Eng.* 14:201; Buchwald et al. (1980). *Surgery* 88:507; Saudek et al. (1989). *N. Engl. J. Med.* 321:574). In another embodiment, polymeric materials are used. In yet another embodiment a controlled release system is placed in proximity of the therapeutic target thus requiring only a fraction of the systemic dose. In yet another embodiment, a controlled release system is placed in proximity of the therapeutic target, thus requiring only a fraction of the systemic. Other controlled release systems are discussed in the review by Langer (1990). *Science* 249:1527-1533.

In another embodiment, the compositions of the present disclosure (as well as combination compositions separately or together) include those formed by impregnation of the beta-lactamase inhibitor described herein into absorptive materials, such as sutures, bandages, and gauze, or coated onto the surface of solid phase materials, such as surgical staples, zippers and catheters to deliver the compositions. Other delivery systems of this type will be readily apparent to those skilled in the art in view of the instant disclosure.

Dosages

Embodiments of the beta-lactamase inhibitor can be administered to a host in one or more doses. Those of skill will readily appreciate that dose levels can vary as a function of the specific the beta-lactamase inhibitor administered, the severity of the symptoms and the susceptibility of the subject to side effects. Preferred dosages for a given compound are readily determinable by those of skill in the art by a variety of means.

In an embodiment, multiple doses of the beta-lactamase inhibitor are administered. The frequency of administration of the beta-lactamase inhibitor can vary depending on any of a variety of factors, e.g., severity of the symptoms, and the like. For example, in an embodiment, the beta-lactamase inhibitor can be administered once per month, twice per month, three times per month, every other week (qow), once per week (qw), twice per week (biw), three times per week (tiw), four times per week, five times per week, six times per week, every other day (qod), daily (qd), twice a day (qid), or three times a day (tid). As discussed above, in an embodiment, the beta-lactamase inhibitor is administered continuously.

The duration of administration of the beta-lactamase inhibitor analogue, e.g., the period of time over which the beta-lactamase inhibitor is administered, can vary, depending on any of a variety of factors, e.g., patient response, etc. For example, the beta-lactamase inhibitor in combination or separately, can be administered over a period of time of about one day to one week, about two weeks to four weeks, about one month to two months, about two months to four months, about four months to six months, about six months to eight months, about eight months to 1 year, about 1 year to 2 years, or about 2 years to 4 years, or more.

Routes of Administration

Embodiments of the present disclosure provide methods and compositions for the administration of the active agent (e.g., the beta-lactamase inhibitor) to a host (e.g., a human) using any available method and route suitable for drug delivery, including in vivo and ex vivo methods, as well as systemic and localized routes of administration.

Routes of administration include intranasal, intramuscular, intratracheal, subcutaneous, intradermal, topical application, intravenous, rectal, nasal, oral, and other enteral and parenteral routes of administration. Routes of administration may be combined, if desired, or adjusted depending upon the agent and/or the desired effect. An active agent (e.g., the beta-lactamase inhibitor) can be administered in a single dose or in multiple doses.

Embodiments of the beta-lactamase inhibitor can be administered to a host using available conventional methods and routes suitable for delivery of conventional drugs, including systemic or localized routes. In general, routes of administration contemplated by the disclosure include, but are not limited to, enteral, parenteral, or inhalational routes.

Parenteral routes of administration other than inhalation administration include, but are not limited to, topical, transdermal, subcutaneous, intramuscular, intraorbital, intracapsular, intraspinal, intrasternal, and intravenous routes, i.e., any route of administration other than through the alimentary canal. Parenteral administration can be conducted to effect systemic or local delivery of the beta-lactamase inhibitor. Where systemic delivery is desired, administration typically involves invasive or systemically absorbed topical or mucosal administration of pharmaceutical preparations.

In an embodiment, the beta-lactamase inhibitor can also be delivered to the subject by enteral administration. Enteral routes of administration include, but are not limited to, oral and rectal (e.g., using a suppository) delivery.

Methods of administration of the beta-lactamase inhibitor through the skin or mucosa include, but are not limited to, topical application of a suitable pharmaceutical preparation, transdermal transmission, injection and epidermal administration. For transdermal transmission, absorption promoters or iontophoresis are suitable methods. Iontophoretic transmission may be accomplished using commercially available "patches" that deliver their product continuously via electric pulses through unbroken skin for periods of several days or more.

While embodiments of the present disclosure are described in connection with the Examples and the corresponding text and figures, there is no intent to limit the disclosure to the embodiments in these descriptions. On the contrary, the intent is to cover all alternatives, modifications, and equivalents included within the spirit and scope of embodiments of the present disclosure.

EXAMPLES

Example 1

Introduction

Beta-lactam compounds such as penicillins are the most widely used antibiotics due to their effective inhibition of the transpeptidases required for bacterial cell wall synthesis[1-3]. Beta-lactamases catalyze β-lactam hydrolysis and are primary mediators of bacterial resistance to these compounds[4, 5]. There are four β-lactamase families, Classes A to D, among which Classes A and C are the most commonly observed in the clinic[6, 7]. CTX-M is a new group of Class A β-lactamases that is particularly effective against the extended spectrum β-lactam antibiotics such as cefotaxime[8-12], which itself was developed to counter bacterial resistance to first-generation penicillins and cephalosporins. The widespread emergence of extended spectrum beta-lactamase (ESBL) such as CTX-M will continue to limit treatment options for bacterial infections. Since its discovery in the 1990s, CTX-M has become the most frequently observed ESBL in many regions of the world.

The use of a β-lactamase inhibitor in combination with a β-lactam antibiotic is a well-established strategy to counter resistance[13]. Existing β-lactamase inhibitors (e.g., clavulanic acid) generally also contain a β-lactam ring, making them susceptible to resistance stemming from up-regulation of β-lactamase production, selection for new β-lactamases, and other mechanisms evolved over millions of years' chemical warfare between bacteria and β-lactam producing microorganisms[14-17]. In principle, these problems can be overcome by developing structurally novel (non-β-lactam) inhibitors of β-lactamases.

We recently described our application of fragment-based molecular docking to identify a new class of non-covalent inhibitors of CTX-M β-lactamase.[18] The fragment-based approach allowed us to overcome the limited chemical diversity of lead/drug-sized compound libraries, which presents a particularly challenging problem for antibiotic discovery. This is due to the starkly different chemical features of antibiotics when compared to drugs targeting human proteins such as GPCRs, towards which most HTS screening libraries are inherently biased[19, 20] Thus, our virtual screening of fragment libraries led to the discovery of a tetrazole-based inhibitor chemotype, represented by compound 1, at the time the highest affinity (Ki=21 μM) non-covalent inhibitor of any Class A β-lactamase (FIG. 4, Table 1). The tetrazole-based chemotype appealed to us for several reasons. First, the tetrazole group has excellent shape and electrostatic complementarity with the active site subpocket of CTX-M that usually binds the C(3)4' carboxylate of traditional β-lactam antibiotics (FIG. 1). Second, the tetrazole ring is a well-known binding bioisostere for carboxylate groups that often possesses more favorable pharmacokinetics properties.

Close examination of the complex crystal structure with compound 1 revealed two potential binding hot spots that might be exploited to improve affinity (FIG. 1). The first is a relatively non-polar binding surface surrounding Pro167, while the second site, constituting Asp240 suggested the possibility of introducing a favorable electrostatic interaction. The design and synthesis of compounds that focused on interacting with these binding hotspots has resulted in several novel high affinity non-covalent inhibitors. The binding of many new inhibitors to the CTX-M active site was further investigated using X-ray crystallography (FIG. 7). Targeting both hot spots with small substituents allowed us to identify more ligand-efficient inhibitors, including the highest affinity (Ki=89 nM) non-covalent inhibitor of a Class A β-lactamase reported to date.

Results:

Structure Based Design

Compound 1 as well as other less potent inhibitors were identified by a molecular docking screen of the ZINC lead-like database using the program DOCK.[18, 21-23] In the complex crystal structure of 1 with CTX-M, the fluoro-benzene ring is in close proximity to Asp240 and the binding surface surrounding Pro167. Two carbon atoms on the fluoro-benzene ring are in van der Waals contact (3.43 Å) with the Oδ1 atom of Asp240. Although there are favorable electrostatic interactions between the ring hydrogen atoms of 1 and Asp240 Oδ1, we hypothesized that a hydrogen bonding interaction or a salt bridge to Asp240 in a modified ligand would greatly enhance binding affinity. In a previously determined complex structure with a boronic acid inhibitor bearing ceftazidime side chain (pdb ID 1YLY)[9], Asp240 has been observed to form such a hydrogen bond with the ligand's distal amine group, which may partly accounts for the improved CTX-M activity against ceftazidime. Meanwhile, the fluorine atom of compound 1 is 4-5 Å away from a cluster of protein carbon atoms including Pro167Cβ, Pro167Cγ, Pro157C, Thr168Cα and Thr171Cγ, suggesting that more favorable van der Waals contacts and hydrophobic interactions could be formed between this site and analogs modified at the three position of the aryl ring. Hence, based on these observations from the complex structure of 1, two series of analogs independently targeting each of the two potential binding hot spots were designed, docked and synthesized.

Synthesis

The simple achiral structure of 1 is an attractive feature of this chemotype as compared to traditional β-lactamase inhibitors. Designed analogs that docked well to CTX-M computationally were synthesized in 1-3 synthetic steps, or in some cases could be purchased commercially. Thus, reaction of commercially available 3-(1H-tetrazol-5-yl)aniline with various commercial or synthesized carboxylic acids or acid chlorides afforded the final analogs. Our initial designs focused exclusively on the 3-fluoro aryl ring of 1 as this moiety is in proximity to both of the putative binding hot spots we sought to target. The aryl tetrazole moiety of 1 appears highly complementary to its binding site already and was thus viewed as a structural anchor that would be unlikely to bind much differently in the new analogs. This prediction was borne out when complex structures of new analogs were solved, as detailed later.

Enzymology and Binding Affinities To investigate the effectiveness of the new analogs, we employed CTX-M-9 and a UV-absorbance based biochemical assay to obtain binding affinities. A series of analogs with modifications at the three positions were evaluated with the expectation that these compounds would form more favorable non-polar contacts with Pro167 (Table 1, FIG. 4). Compounds 2-11 possess 3-substituents of roughly increasing size and with generally lipophilic character, though not exclusively so. Interestingly, all of these modified analogs proved superior to 1 in terms of Ki, but the most ligand-efficient analogs were those possessing roughly spheroid hydrophobes (e.g., Me, Br, $CF_3$). The highest affinity compound from the series targeting Pro167 was the 3-trifluoromethyl compound 10, with a Ki of 2.4 µM (Table 1, FIG. 4). Analogs 6-8 bearing less hydrophobic and non-spheroid substituents had similar ligand efficiency as 1 but superior LipE values (1.37 for 1 vs. 2.51 for 7). The parameter LipE (defined as log Ki-c log P)[24] provides a measure of binding affinity improvement achieved while retaining favorable physiochemical properties. A surprising result was that even large substituents (2-pyrimidyl, compound 11) could be tolerated at the 3-position, although ligand efficiency suffers. A complex crystal structure of 11 confirmed a similar binding pose as 1 (see below) so the reduced ligand efficiency of this analog perhaps reflects a steric clash and/or unfavorable desolvation energy associated with the burial of a pyrimidine ring nitrogen atom.

To target the second hotspot comprising the area around Asp240, we designed analogs bearing hydrogen bond donors and/or charged side chains at various positions on the aryl ring. These various designs were docked to CTX-M and the best-scoring analogs were synthesized and tested in the biochemical assay (Table 2, FIG. 5). Our attempt to form a salt bridge to Asp240 by the introduction of a basic dimethylamino side chain (compound 12) was unsuccessful, the analog possessing only modest affinity (Ki=76 µM). The regioisomeric aryl nitriles 13 and 14 had very different affinities, with meta-substitution as in 14 preferred (Ki=7.2 µM). By far the most interesting analogs from this series (Ki~1 µM) were the heterocyclic analogs 16-18, each of which possesses a potential hydrogen bond donor in a position (pseudo meta or para) predicted by docking to be in close proximity to Asp240. Compounds 16-18 moreover exhibited improved ligand efficiency (0.34-0.35) and LipE values (2.59-3.58) as compared to 1 (0.31 and 1.37).

From these initial two libraries, we concluded that the independent targeting of each binding hotspot (Asp240 and Pro167) could indeed be leveraged to produce more potent and ligand-efficient inhibitors. As described below, the design principles and predicted binding poses of these initial analogs were validated by the solution of complex crystal structures for representative examples. Having identified more favorable binding elements for both hotspots, the logical next step was to combine theses to produce inhibitors that targeted both sites simultaneously (Table 3, FIG. 6). Indeed, the combination of a benzimidazole ring as in 16 with a trifluoromethyl substituent as in 10, afforded analog 19, the most potent analog yet identified (Ki=89 nM; L.E.=0.36; LipE=3.86). We expected that the benzimidazole ring in 19 might contribute an important hydrogen bond to Asp240 and therefore explored whether simple hydroxyl or amino substituents in this position could function similarly (analogs 20-22). These analogs were indeed more potent than the direct comparators 4 and 10 which lack a hydrogen bond donor, but 20-22 were not as potent as 19. As detailed later, the solution of a complex structure of benzimidazole analog 16 revealed additional contacts that may explain the improved potency of benzimidazole 19 as compared to 20 and 22. Unexpectedly, the fluoro benzimidazole analog 23 was only equipotent to des-fluoro comparator 16, the flouro substituent apparently not providing any additional affinity via putative interaction with Pro167. Perhaps tighter association of the benzimidazole ring with Asp240 draws the ligand slightly away from Pro167, thus requiring a larger substituent (such as trifluoromethyl in 19) to productively contact Pro167.

X-Ray Crystallographic Structure Determination

The structural details of the interactions between CTX-M-9 and several of the new analogs were investigated in order to gain an understanding of the molecular basis for the binding affinity improvement and facilitate future inhibitor development. Complex crystal structures with CTX-M-9 were determined to a resolution in the range of 1.2-1.4 Å, where the ligand binding pose can be determined unambiguously. In all of these structures, the inhibitor adopts a single pose, as shown by the unbiased 2Fo-Fc electron densities.

Figure 2A:
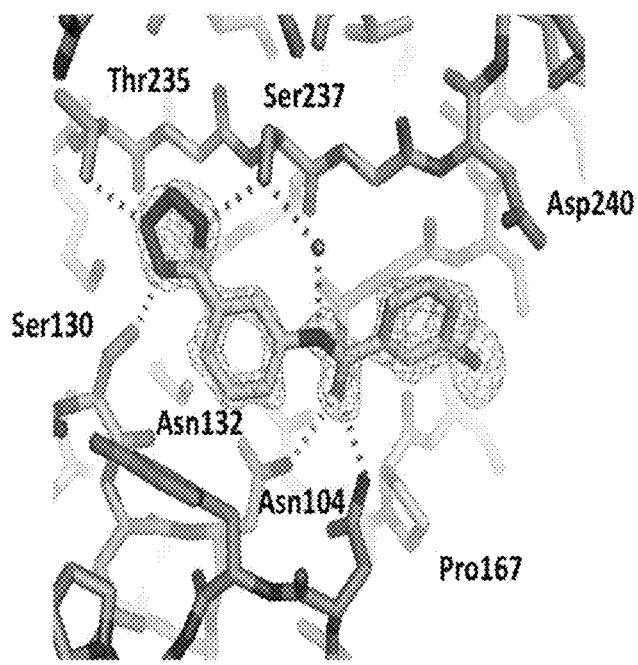
FIGS. 2A-C illustrate crystal complex structures with compounds targeting Pro167.
Figure 2B:
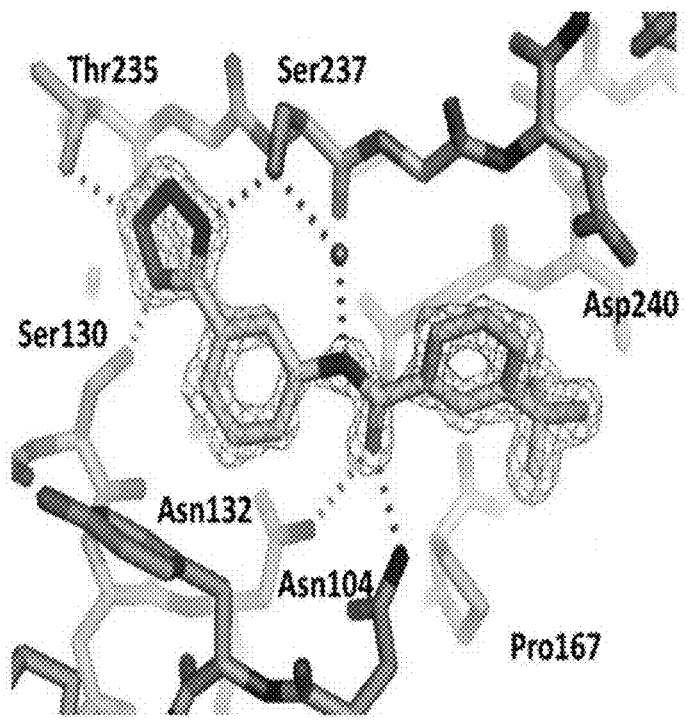
Figure 2C:
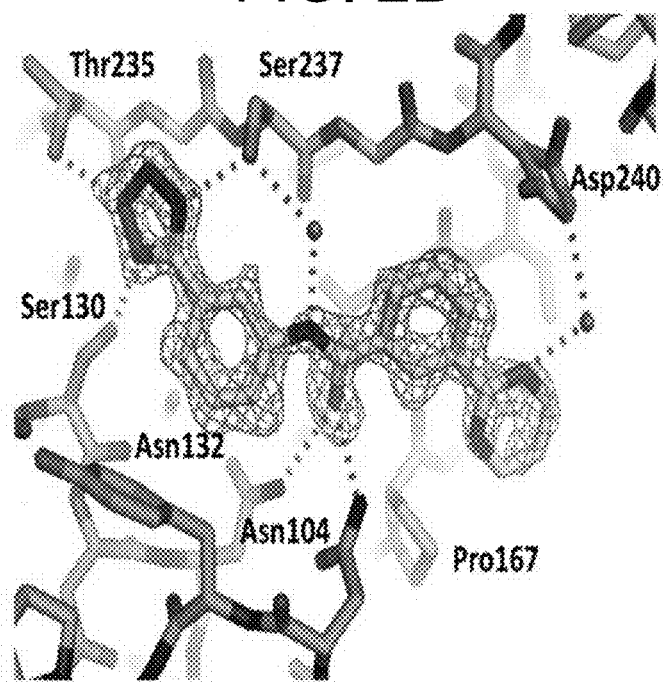

FIGS. 2A-C show the X-ray crystal structures of compounds 4, 10, and 11 in the active site of CTX-M-9; these compounds were designed to make significant non-polar interactions with Pro167. The size increase in the bulkier side substituents such as trifluoromethyl is demonstrated in their larger electron density volumes, compared with that of the fluorine atom in 1. In the larger sense, the atoms of the new ligands make similar contacts with the surrounding active site atoms as does 1. For instance, compounds 4, 10, and 11 (FIG. 2A-C) all form hydrogen bonds between the tetrazole ring and Thr235, Ser237, and Ser130 from the protein, which is similar to compound 1 (FIG. 1, Table 1). They also share the characteristic water-mediated interaction between the amide linkage and Ser237, as well as two hydrogen bonds with Asn132 or Asn104. The contacts between the distal benzene ring and Asp240, as observed in compound 1, are maintained in compounds 4 and 10, with two ring carbon atoms in vdw contact and approximately 3.2-3.3 Å away from the Oδ1 atom of Asp240. The favorable contacts between Pro167 and the functional groups on 4 and 10 are evident. The bromine atom on the ring structure of 4 is 4-5 Å away from the cluster of protein carbon atoms including Pro167Cβ, Pro167Cγ, Pro167C, Thr168Cα, and Thr171Cγ. Likewise, the three branched fluorine atoms of compound 10 are in close vdw contacts with these protein carbon atoms, which are approximately 3.4-3.8 Å away. The binding of compound 11, on the other hand, differs slightly from compounds 1, 4 and 10 in these regions (FIG. 2C). The pyrimidine ring forms a water-mediated interaction with Asp240 and induces Asp240 to adopt a new conformation (FIG. 2A-C). This water-mediated contact exists in the complex structure only with partial occupancy, as suggested by the relatively weak electron density of the water (2 σ) and the presence of two Asp240 conformations including the one previously observed in apo and other complex structures. There is vdw contact observed between the carbon atoms of the pyrimidine ring in 11 and Pro167Cγ, Thr168Cγ, Thr171Cγ, which are 3.3-3.6 Å distant. Despite the water-mediated hydrogen bond and vdw contacts between the ring carbon atoms and Pro167 and Thr168, the affinity of compound 11 is less than for 4 or 10; this may be due to the burial of a polar pyrimidine ring nitrogen atom and electrostatic repulsion between this nitrogen and Pro167O. Additionally, the vdw contacts described above may be slightly too close for the optimal carbon-carbon distance in vdw interaction (~4 Å) and thus suggest possible minor steric clash.

Figure 3A:
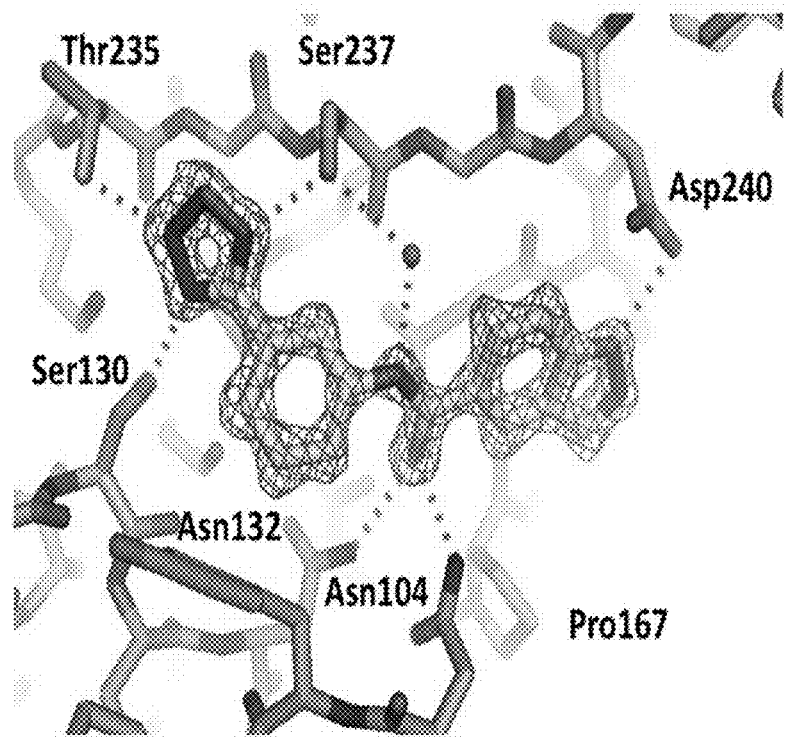
FIGS. 3A-C illustrate crystal complex structures with compounds targeting Asp240.
Figure 3B:
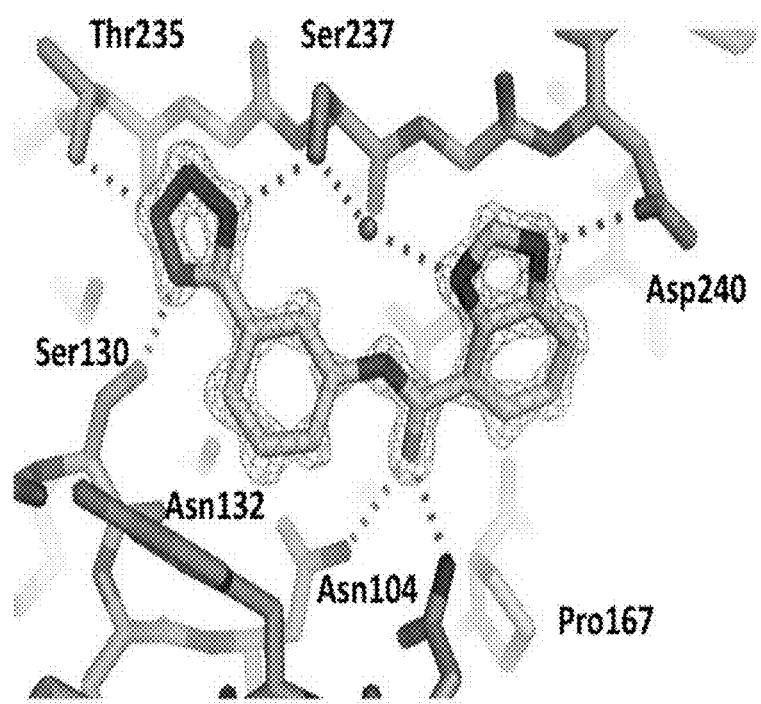
Figure 3C:
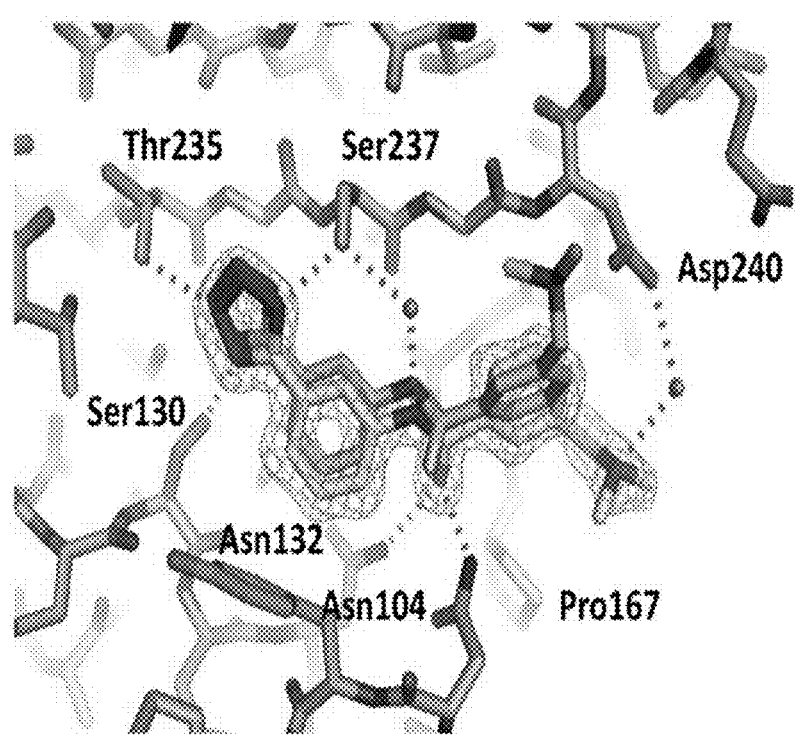

Crystal structures were also obtained for compounds designed to establish polar interactions with Asp240, including compounds 12, 16, and 18. Again the core structure of these compounds, including the tetrazole ring and the amide bond, establishes contacts with Ser130, Thr235, Ser237, Asn104 and Asn132 similar to compound 1 (FIG. 3A-C). Both compounds 16 and 18 form a direct hydrogen bond with Asp240 as designed. Compound 16 has in addition a favorable contact between N-1/C-2/N-3 of the benzimidazole ring and the main chain atoms around Gly238, while compound 18 establishes more vdw interactions with Pro167 and Thr168. Benzimidazole 16 and indaole 15 both contact Asp240 through a hydrogen bond from N-1. The additional ring nitrogen (N-3) in 16 appears to form a water-mediated hydrogen bonding contact with Ser237 (FIG. 3B). The electron density for the water molecule contacting N-3 in 16 is weaker (2.4 σ) than other structural waters in the active site, perhaps explaining why the presence of this additional interaction in 16 does not significantly improve potency in comparison to 15. Alternatively, the modest additional affinity of compound 16 may originate from an intramolecular hydrogen bond between N-3 and the proximal amide N—H, which stabilizes the conformation conducive to a hydrogen bond between the compound and Asp240.

FIG. 3C shows the discrepancy between the designed interaction of compound 12 with Asp240 (in cyan) and its actual interactions observed in the crystal structure (in light gray). Initially, we designed compound 12 to form a salt bridge with Asp240. However, the X-ray crystal structure reveals the actual binding pose in which a water-mediated hydrogen bond is formed between the positively charged side chain and Asp240. The new side chain is cradled in the small pocket surrounding Pro167, underscoring once again the potential of this binding surface in establishing new interactions with future inhibitors.

Discussion

The identification of novel non-covalent inhibitors of class A β-lactamases is a promising new approach to maintain the effectiveness of β-lactam antibiotics. A purpose of this initial study was to rapidly identify regions of the active site that could be more productively engaged with designed ligands, thus enabling further optimization of tetrazole-based inhibitors of CTX-M β-lactamase. The surgical introduction of new functional groups in the distal ring of 1 succeeded in producing improved analogs that make both non-polar and polar contacts with CTX-M β-lactamase, improving affinity ~200-fold whilst retaining good lead-like properties (reflected in notably improved LipE values). The results confirm the importance of Pro167 and Asp240 as binding hotspots in CTX-M β-lactamase and demonstrate the tractability of the novel tetrazole inhibitor chemotype.

Both Pro167 and Asp240 have been observed to interact with β-lactam substrates or covalent inhibitors in complex structures with CTX-M-9. In a recent crystal structure of CTX-M-9 S70G mutant and cefotaxime (pdb code 3HLW)[12], the amino group on the aminothiazole ring of cefotaxime forms a hydrogen bond with Asp240 while the methoxyimino group nestles comfortably in the subpocket around Pro167. Compared with the apo structure, such interactions cause small shifts in atom positions for residues in this area (e.g., ~0.5 Å for Asp240Cα), a conformational change not observed in complex structures with smaller substrates such as benzylpenicillin. Similar hydrogen bonds with Asp240 have also been found in previous complex structures with boronic acid inhibitors[9, 12]. Additionally, Pro167 and Asp240 are conserved in other CTX-M type enzymes such as Toho-1[25-27]. In the acyl-enzyme complex structure of Toho-1 Glu166A mutant with cefotaxime (pdb ID, 1IYO)[26], the aminothiazole ring makes both a direct and a water-mediated hydrogen bond with Asp240 while establishing vdw interactions with Pro167. Together with our experiments, these observations suggest both Asp240 and Pro167 are binding hot spots useful for inhibitor design against CTX-M β-lactamases.

Even more significantly, it is also possible to consider using similar hot spot targets against other Class A β-lactamases. For narrow-spectrum β-lactamases such as TEM-1 and SHV-2, residue 240 is a glutamate. Although it has been hypothesized that the substitution of Glu240 for Asp may enlarge the active site and allow ESBLs such as CTX-M to accommodate the bulkier side chains of cefotaxime and other third-generation cephalosporins, both Glu240 and Asp240 present similar features in the protein binding pocket, including the net negative charge and the nearly identical positioning of one oxygen atom from the carboxylate group. Comparing the complex structures between a ceftazidime-like boronic acid inhibitor and CTX-M-9 (pdb ID, 1YLY) to that of the same compound with TEM-1 (pdb ID 1M40) shows that the aminothiazole ring of the inhibitor is placed in similar positions and forms a hydrogen bond with residue 240 in both structures[9, 28]. Additionally, comparing the affinity of compound 19 with those of compounds 21 and 22 suggests that interactions with the main chain atoms around Gly238, the residue immediately preceding Asp240 (note the numbering gap due to convention), may also contribute significantly to binding. Gly238 is highly conserved in CTX-M, TEM and SHV enzymes. Meanwhile, the non-polar binding surface around residue 167 is also largely conserved in these β-lactamases. Like CTX-M, TEM-1 has a proline in this position. Although it is replaced by a threonine in SHV enzymes, most of the carbon atoms, like Cα, Cβ atoms of residues 167 and 168, are in similar positions and thus form a binding subpocket with features comparable to that in CTX-M, albeit with some new features such as Thr167Oγ. In the crystal structure between cefoperazone and SHV-1, the carbon atoms of the compound's piperazine ring are in van der Waals contacts with the Cβ and C atoms of Thr167[29].

In addition to revealing the importance of Pro167 and Asp240 in ligand binding, the rapid evolution of compound 1 into nanomolar inhibitors like 19 demonstrates the tractability of the tetrazole chemotype as a lead scaffold. The five-member tetrazole ring displays both good shape and electrostatic complementarity with a subpocket usually occupied by the C(3)4' carboxylate group of β-lactam compounds, forming three hydrogen bonds with Ser130, Thr235 and Ser237 while being stacked against the peptide bond between Thr235 and Gly236. Several key features of this binding subpocket are also present in the active site of AmpC Class C β-lactamase. For example, Thr235 and Gly 236 are conserved in AmpC (Thr316 and Gly317). Tyr150, a key catalytic residue in AmpC, places its hydroxyl group in a position similar to that of Ser130 in CTX-M. Other common features shared by the active sites of Class A and C enzymes may further allow the design of inhibitors with broader spectrum. For instance, existing covalent inhibitors against both classes of enzymes almost invariantly place an oxygen atom in the oxyanion hole formed by two backbone amide groups. This binding hot spot is occupied instead by a water molecule in the complex structures of our current tetrazole-based inhibitors. The identification of tetrazolestype inhibitors that suitably occupy the oxyanion hole may expand the utility of this chemotype to target a wider range of β-lactamases. Such expanded spectrum compounds may also have greater potential for cellular activity against resistant bacteria. So far the inhibitors from the current study were unable to reverse β-lactam resistance in *E. coli* strains expressing CTX-M β-lactamase (data not shown). Whether this reflects a lack of sufficient potency or other factors such as poor permeability or active efflux from the bacterium are questions we are actively pursuing.

Conclusions

Structurally-guided optimization of a novel-class of CTX-M β-lactamase inhibitors has confirmed two binding hotspots that can be targeted in the search for higher affinity inhibitors. Importantly, these hotspots are shared by other therapeutically important groups of β-lactamases, suggesting the potential for tetrazole-class inhibitors with an expanded spectrum of β-lactamase activity. More generally, the approaches we have used to identify and optimize novel non-covalent inhibitors of CTX-M can be effectively used to identify additional classes of inhibitors for other β-lactamases. In conclusion, the nanomolar potency of 19 distinguishes this compound as the highest-affinity non-covalent inhibitor yet identified for a Class A β-lactamase. Current efforts are focused on further elaborating the tetrazole chemotype with a goal of producing a novel class of compounds effective against a wide range of clinically relevant β-lactamases.

Experimental Methods

Compound Docking

Molecular docking was used as previously described[18] to evaluate newly designed compounds or existing ones from ZINC small-molecule database with the program DOCK 3.5.54[18, 21-23].

Synthesis

General Methods $^1$H NMR spectra were recorded on a Varian INOVA-400 400 MHz spectrometer. Chemical shifts are reported in δ units (ppm) relative to TMS as an internal standard. Coupling constants (J) are reported in hertz (Hz). The known compounds 1, 2, 3, 4, 6, 8, 10 and 13[30] were prepared according the general procedures and/or were obtained from commercial sources (Ryan Scientific, TimTec). All other reagents and solvents were purchased from Aldrich Chemical, Acros Organics, Enamine, Alfa Aesar, Apollo Scientific and used as received. Air and/or moisture sensitive reactions were carried out under an argon atmosphere in oven-dried glassware using anhydrous solvents from commercial suppliers. Air and/or moisture sensitive reagents were transferred via syringe or cannula and were introduced into reaction vessels through rubber septa. Solvent removal was accomplished with a rotary evaporator at ca. 10-50 Torr. Column chromatography was carried out using a Biotage SP1 flash chromatography system and silica gel cartridges from Biotage. Analytical TLC plates from EM Science (Silica Gel 60 F254) were employed for TLC analyses. Microwave heating was accomplished using a CEM reaction microwave. Hydrogenation reactions were carried out with a ThalesNano H-Cube hydrogenator.

All synthesized analogs tested against CTX-M were judged to be of 95% or higher purity based on analytical LC/MS analysis. LC/MS analyses were performed on a Waters Micromass ZQ/Waters 2795 Separation Module/Waters 2996 Photodiode Array Detector system controlled by MassLynx 4.0 software. Separations were carried out on an XTerra® MS $C_{18}$ 5 μm 4.6×50 mm column at ambient temperature using a mobile phase of water-acetonitrile containing 0.05% trifluoroacetic acid. Gradient elution was employed wherein the acetonitrile-water ratio was increased linearly from 5 to 95% acetonitrile over 2.5 minutes, then maintained at 95% acetonitrile for 1.5 min., and then decreased to 5% acetonitrile over 0.5 min, and maintained at 5% acetonitrile for 0.5 min. Compound purity was determined by integrating peak areas of the liquid chromatogram, monitored at 254 nm.

General Procedure A.

An oven-dried vial or flask is charged with 3-(1H-tetrazol-5-yl)aniline (1 equiv), the appropriate carboxylic acid (1 equiv), 1-ethyl-3-[3-dimethylaminopropyl]carbodiimide hydrochloride (1.5 equiv), 1-hydroxybenzotriazole (1.5 equiv) and N,N'-diisopropylethylamine (2 equiv) and stirred in DMF (0.5 mL) at room temperature for 24 h or until judged complete by LC/MS analysis. The reaction mixture is diluted with water (2 mL) and after adjusting the pH to ~2 with 1N HCl, the mixture is extracted with ethyl acetate. The organic extracts are washed with brine, dried over magnesium sulfate and concentrated under reduced pressure. The crude material thus obtained is purified by reverse phase HPLC to afford the desired product.

General Procedure B.

An oven-dried vial or flask is charged with 3-(1H-tetrazol-5-yl)aniline (1 equiv), the appropriate acid chloride (1.05 equiv) and N,N'-diisopropylethylamine (2 equiv) and stirred in dichloromethane (5 mL) at room temperature for 30 min. The reaction mixture is diluted with dichloromethane and washed with water. After adjusting the pH to ~2 with 1N HCl, the mixture is extracted with ethyl acetate. The organic extracts are washed with brine, dried over magnesium sulfate and concentrated under reduced pressure. The crude material thus obtained is purified by flash column chromatography (5-20% methanol/dichloromethane).

3-Cyclopropyl-N-[3-(1H-tetrazol-5-yl)-phenyl]-benzamide (5)

3-(1H-Tetrazol-5-yl)aniline was reacted with commercially available 3-cyclopropylbenzoic acid according to general procedure A to afford the title compound in 63% yield; $^1$H NMR (DMSO-$d_6$) δ 10.42 (s, 1H), 8.55 (s, 1H), 7.93 (d, J=8 Hz, 1H), 7.72 (d, J=8 Hz, 2H), 7.65 (s, 1H), 7.56 (t, J=8 Hz, 1H), 7.39 (t, J=8 Hz, 1H), 7.29 (d, J=8 Hz, 1H), 1.97-2.03 (m, 1H), 0.97-1.01 (m, 2H), 0.74-0.78 (m, 2H); LCMS (ESI) m/z 306 (MH+).

3-Acetyl-N-[3-(1H-tetrazol-5-yl)-phenyl]-benzamide (7)

3-(1H-Tetrazol-5-yl)aniline was reacted with commercially available 3-acetylbenzoic acid according to general procedure A to afford the title compound in 33% yield; $^1$H NMR (DMSO-$d_6$) δ 10.67 (s, 1H), 8.57 (s, 1H), 8.52 (s, 1H), 8.22 (d, J=8 Hz, 1H), 8.16 (d, J=8 Hz, 1H) 7.96 (d, J=8 Hz, 1H), 7.75 (d, J=8 Hz, 1H), 7.70 (t, J=8 Hz, 1H), 7.59 (t, J=8 Hz, 1H), 2.65 (s, 3H); LCMS (ESI) m/z 308 (MH+).

N-[3-(1H-Tetrazol-5-yl)-phenyl]-isophthalamic acid methyl ester (9)

3-(1H-Tetrazol-5-yl)aniline was reacted with commercially available mono-methylisophthalate according to general procedure A to afford the title compound in 22% yield; $^1$H NMR (DMSO-$d_6$) δ 10.70 (s, 1H), 8.56 (s, 2H), 8.25 (d, J=8 Hz, 1H), 8.16 (d, J=8 Hz, 1H) 7.96 (d, J=8 Hz, 1H), 7.68-7.75 (m, 2H), 7.58 (t, J=8 Hz, 1H), 3.90 (s, 3H); LCMS (ESI) m/z 324 (MH+).

3-Cyano-N-[3-(1H-tetrazol-5-yl)-phenyl]-benzamide (14)

3-(1H-Tetrazol-5-yl)aniline was reacted with commercially available 3-cyanobenzoic acid according to general procedure A and purified by flash column chromatography (5-15% methanol/dichloromethane) to afford the title compound in 66% yield; $^1$H NMR (DMSO-$d_6$) δ 10.63 (s, 1H), 8.53 (s, 1H), 8.43 (s, 1H), 8.25 (d, J=8 Hz, 1H), 8.06 (d, J=8 Hz, 1H) 7.92 (d, J=8 Hz, 1H), 7.75 (d, J=8 Hz, 2H), 7.56 (t, J=8 Hz, 1H); LCMS (ESI) m/z 291 (MH+).

1H-Indole-4-carboxylic acid [3-(1H-tetrazol-5-yl)-phenyl]-amide (15)

3-(1H-Tetrazol-5-yl)aniline was reacted with commercially available indole-4-carboxylic acid according to general procedure A to afford the title compound in 10% yield; $^1$H NMR (DMSO-$d_6$) δ 11.35 (s, 1H), 10.41 (s, 1H), 8.65 (s, 1H), 7.93 (d, J=8 Hz, 1H), 7.70 (d, J=4 Hz, 1H), 7.53-7.62 (m, 3H), 7.47 (s, 1H), 7.20 (t, J=8 Hz, 1H), 6.85 (s, 1H); LCMS (ESI) m/z 305 (MH+).

3H-Benzoimidazole-4-carboxylic acid [3-(1H-tetrazol-5-yl)-phenyl]-amide (16)

3-(1H-Tetrazol-5-yl)aniline (75 mg, 0.47 mmol), 1H-benzimidazole-4-carboxylic acid (76 mg, 0.47 mmol), 1-ethyl-3-[3-dimethylaminopropyl]carbodiimide hydrochloride (135 mg, 0.7 mmol), 1-hydroxybenzotriazole (95 mg, 0.7 mmol) and N,N'-diisopropylethylamine (0.17 mL, 0.94 mmol) was stirred in DMF (0.5 mL) at room temperature for 24 h. The reaction mixture is diluted with water (2 mL) and after approximately adjusting the pH to 4 with 1N HCl, the mixture was extracted with ethyl acetate. The organic extracts were washed with brine, dried over magnesium sulfate and concentrated under reduced pressure. The crude material was purified by reverse phase HPLC to afford the product as a trifluoroacetic acid salt in 5% yield. $^1$H NMR (DMSO-$d_6$) δ 8.62 (s, 1H), 8.53 (s, 1H), 7.99-8.02 (m, 3H), 7.86 (d, J=8 Hz, 1H), 7.77 (d, J=4 Hz, 1H), 7.62 (t, J=8 Hz, 1H), 7.43 (t, J=8 Hz, 1H), 7.04 (s, 1H); LCMS (ESI) m/z 306 (MH+).

1H-Indole-5-carboxylic acid [3-(1H-tetrazol-5-yl)-phenyl]-amide (17)

3-(1H-Tetrazol-5-yl)aniline was reacted with commercially available indole-5-carboxylic acid according to the general procedure A to afford the title compound in 9% yield; $^1$H NMR (DMSO-$d_6$) δ 11.39 (s, 1H), 10.36 (s, 1H), 8.62 (s, 1H), 8.30 (s, 1H), 7.96 (d, J=8 Hz, 1H), 7.75 (d, J=8 Hz, 1H), 7.69 (d, J=8 Hz, 1H), 7.45-7.57 (m, 3H), 6.58 (s, 1H); LCMS (ESI) m/z 305 (MH+).

1H-Indazole-5-carboxylic acid [3-(1H-tetrazol-5-yl)-phenyl]-amide (18)

3-(1H-Tetrazol-5-yl)aniline was reacted with commercially available indazole-5-carboxylic acid according to general procedure A to afford the title compound in 6% yield; $^1$H NMR (DMSO-$d_6$) δ 10.50 (s, 1H), 8.61 (s, 1H), 8.51 (s, 1H), 8.26 (s, 1H), 7.95-7.98 (m, 3H), 7.71 (d, J=4 Hz, 1H), 7.64 (d, J=8 Hz, 1H), 7.57 (t, J=8 Hz, 1H); LCMS (ESI) m/z 306 (MH+).

6-Trifluoromethyl-3H-benzoimidazole-4-carboxylic acid [3-(1H-tetrazol-5-yl)-phenyl]-amide (19)

3-(1H-Tetrazol-5-yl)aniline (15 mg, 0.09 mmol), 6-trifluromethyl-benzimidazole-4-carboxylic acid (intermediate 27, 25 mg, 0.09 mmol), 1-ethyl-3-[3-dimethylaminopropyl] carbodiimide hydrochloride (26 mg, 0.135 mmol), 1-hydroxybenzotriazole (18 mg, 0.135 mmol) and N,N'-diisopropylethylamine (0.047 mL, 0.27 mmol) were stirred in DMF (0.2 mL) at room temperature for 24 h. The reaction mixture was filtered and purified by reverse phase HPLC to afford the title compound as a trifluoroacetic acid salt in 30% yield; $^1$H NMR (DMSO-$d_6$) δ 8.78 (s, 1H), 8.54 (s, 1H), 8.24 (d, J=12 Hz, 2H), 8.02 (d, J=8 Hz, 1H), 7.80 (d, J=8 Hz, 1H), 7.64 (t, J=8 Hz, 1H); LCMS (ESI) m/z 374 (MH+).

3-Bromo-5-hydroxy-N-[3-(1H-tetrazol-5-yl)-phenyl]-benzamide (20)

3-(1H-Tetrazol-5-yl)aniline was reacted with commercially available 3-bromo-5-hydroxybenzoic acid according to general procedure A to afford the title compound in 22% yield; $^1$H NMR (DMSO-$d_6$) δ 10.48 (s, 1H), 10.27 (s, 1H), 8.55 (s, 1H), 7.91 (d, J=8 Hz, 1H), 7.72 (d, J=4 Hz, 1H), 7.60 (s, 1H), 7.56 (d, J=8 Hz, 1H), 7.34 (s, 1H), 7.15 (s, 1H); LCMS (ESI) m/z 361 (MH+).

3-Hydroxy-N-[3-(1H-tetrazol-5-yl)-phenyl]-5-trifluoromethyl-benzamide (21)

3-(1H-Tetrazol-5-yl)aniline was reacted with commercially available 3-hydroxy-5-trifluoromethyl carboxylic acid according to general procedure A to afford the title compound in 24% yield; $^1$H NMR (DMSO-$d_6$) δ 10.60 (s, 1H), 10.51 (s, 1H), 8.55 (s, 1H), 7.94 (d, J=8 Hz, 1H), 7.74 (d, J=12 Hz, 2H), 7.64 (s, 1H), 7.58 (d, J=8 Hz, 1H), 7.24 (s, 1H); LCMS (ESI) m/z 350 (MH+).

3-Amino-N-[3-(1H-tetrazol-5-yl)-phenyl]-5-trifluoromethyl-benzamide (22)

3-(1H-Tetrazol-5-yl)aniline (75 mg, 0.47 mmol), 3-amino-5-trifluoromethyl-benzoic acid (96 mg, 0.47 mmol), 1-ethyl-3-[3-dimethylaminopropyl]carbodiimide hydrochloride (135 mg, 0.7 mmol), 1-hydroxybenzotriazole (95 mg, 0.7 mmol) and N,N'-diisopropylethylamine (0.16 mL, 0.94 mmol) were stirred in DMF (0.5 mL) at room temperature for 18 h. The reaction mixture was filtered and purified by reverse phase HPLC to afford the title compound in 52% yield; $^1$H NMR (DMSO-$d_6$) δ 10.50 (s, 1H), 8.53 (s, 1H), 7.92 (d, J=8 Hz, 1H), 7.72 (d, J=8 Hz, 1H), 7.56 (t, J=8 Hz, 1H), 7.37 (d, J=8 Hz, 2H), 7.24 (s, 1H); LCMS (ESI) m/z 349 (MH+).

6-Fluoro-3H-benzoimidazole-4-carboxylic acid [3-(1H-tetrazol-5-yl)-phenyl]-amide (23)

3-(1H-Tetrazol-5-yl)aniline was reacted with commercially available 6-fluoro-benzimidazole-4-carboxylic acid according to the general procedure A to afford the title compound in 17% yield; $^1$H NMR (DMSO-$d_6$) δ 8.63 (s, 1H), 8.53 (s, 1H), 7.99 (d, J=8 Hz, 1H), 7.71-7.80 (m, 4H), 7.63 (t, J=8 Hz, 1H); LCMS (ESI) m/z 324 (MH+).

3-Bromo-5-cyano-N-[3-(1H-tetrazol-5-yl)-phenyl]-benzamide (24)

3-(1H-Tetrazol-5-yl)aniline was reacted with commercially available 3-cyano-5-bromobenzoic acid according to the general procedure A to afford the title compound in 24% yield; $^1$H NMR (DMSO-d$_6$) δ 10.70 (s, 1H), 8.53 (s, 1H), 8.45 (s, 1H), 8.41 (d, J=8 Hz, 2H), 7.94 (d, J=8 Hz, 1H), 7.76 (d, J=8 Hz, 1H), 7.59 (t, J=8 Hz, 1H); LCMS (ESI) m/z 370 (MH+).

2-amino 3-nitro-5-trifluoromethylbenzoic acid (25)

Commercially available 2-chloro-3-nitro-5-trifluoromethylbenzoic acid (0.10 g, 0.37 mmol) and aqueous ammonium hydroxide (2 mL) were heated in a sealed tube in a CEM microwave at 120° C. for an hour. After cooling, the pH was adjusted to 2 with 1N HCl. The precipitate was filtered and dried to obtain 2-amino 3-nitro-5-trifluoromethylbenzoic acid as a yellow solid (80 mg). This material was used in the next step without further purification. $^1$H NMR (DMSO-d$_6$) δ 8.49 (s, 1H), 8.32 (s, 1H).

2,3-Diamino-5-trifluromethylbenzoic acid (26)

A solution of 2-amino-3-nitro-5-trifluoromethylbenzoic acid (25, 75 mg, 0.3 mmol) in methanol was passed through a Pd/C cartridge (10 wt %) at a flow rate of 1 mL/min using the H-Cube hydrogenation system. The solution was concentrated under reduced pressure and dried to obtain the title compound (62 mg). This material was used without further purification. $^1$H NMR (CDCl$_3$) δ 7.80 (s, 1H), 7.05 (s, 1H); LCMS (ESI) m/z 221 (MH+).

6-Trifluromethyl-benzimidazole-4-carboxylic acid (27)

Formic acid (0.34 mmol, 3 equiv) was added to intermediate 26 (0.11 mmol, 1 equiv) in aqueous 4M HCl (0.35 mL) and the reaction mixture heated to 100° C. for two hours. The reaction mixture was concentrated under reduced pressure and dried to obtain the title compound (35 mg) as a hydrochloride salt. This material was used without further purification. $^1$H NMR (DMSO-d$_6$) δ 8.74 (s, 1H), 8.33 (s, 1H), 8.07 (s, 1H); LCMS (ESI) m/z 231 (MH+).

General Procedure C.

An oven-dried vial or flask is charged with 3-(1H-tetrazol-5-yl)aniline (1 equiv), the appropriate carboxylic acid (1 equiv), O-(7-azabenzotriazol-1-yl)-N,N,N',N'-tetramethyluronium hexafluorophosphate (1.1 equiv) and N,N'-diisopropylethylamine (2 equiv) and stirred in N,N-dimethylformamide (0.5 mL) at room temperature for 24 h or until judged complete by LC/MS analysis. The mixture is purified by reverse phase HPLC to afford the desired product.

3-(4-Methylphenyl)-N-[3-(1H-1,2,3,4-tetrazol-5-yl)phenyl]-1H-pyrazole-5-carboxamide (28)

3-(1H-Tetrazol-5-yl)aniline was reacted with commercially available 3-(4-methylphenyl)-1H-pyrazole-5-carboxylic acid according to general procedure C to afford the title compound as a trifluoroacetic acid salt in 21% yield; $^1$H NMR (DMSO-d$_6$) δ 10.31 (s, 1H), 8.63 (s, 1H), 7.95 (d, J=6 Hz, 1H), 7.71-7.72 (m, 3H), 7.54 (t, J=6 Hz, 1H), 7.28 (d, J=6 Hz, 1H), 7.16 (s, 1H), 2.32 (s, 3H); LCMS (ESI) m/z 346 (MH+).

3-Phenyl-N-[3-(1H-1,2,3,4-tetrazol-5-yl)phenyl]-1,2-oxazole-5-carboxamide (29)

3-(1H-Tetrazol-5-yl)aniline was reacted with commercially available 3-phenyl-5-isoxazole carboxylic acid according to general procedure C to afford the title compound in 50% yield; $^1$H NMR (DMSO-d$_6$) δ 11.07 (s, 1H), 8.57 (s, 1H), 7.94-7.96 (m, 3H), 7.85 (s, 1H), 7.79 (d, J=6 Hz, 1H), 7.61 (t, J=6 Hz, 1H), 7.53-7.55 (m, 3H); LCMS (ESI) m/z 333 (MH+).

1-Phenyl-N-[3-(1H-1,2,3,4-tetrazol-5-yl)phenyl]-1H-imidazole-4-carboxamide (30)

3-(1H-Tetrazol-5-yl)aniline was reacted with commercially available 1-phenyl-1H-imidazole-4-carboxylic acid according to general procedure C to afford the title compound as a trifluoroacetic acid salt in 21% yield; $^1$H NMR (DMSO-d$_6$) δ 10.25 (s, 1H), 8.67 (s, 1H), 8.48 (d, J=9 Hz, 2H), 7.96 (d, J=6 Hz, 1H), 7.78 (d, J=6 Hz, 2H), 7.70 (d, J=6 Hz, 1H), 7.53-7.57 (m, 3H), 7.42 (t, J=6 Hz, 1H); LCMS (ESI) m/z 332 (MH+).

1-Phenyl-N-[3-(1H-1,2,3,4-tetrazol-5-yl)phenyl]-1H-imidazole-5-carboxamide (31)

3-(1H-Tetrazol-5-yl)aniline was reacted with commercially available 1-phenyl-1H-imidazole-5-carboxylic acid according to general procedure C to afford the title compound as a trifluoroacetic acid salt in 54% yield; $^1$H NMR (DMSO-d$_6$) δ 10.60 (s, 1H), 8.41 (d, J=9 Hz, 2H), 8.04 (s, 1H), 7.76 (d, J=9 Hz, 1H), 7.70 (d, J=6 Hz, 1H), 7.44-7.54 (m, 6H); LCMS (ESI) m/z 332 (MH+).

3-Methyl-N-[3-(1H-1,2,3,4-tetrazol-5-yl)phenyl]-1H-indole-5-carboxamide (32)

3-(1H-Tetrazol-5-yl)aniline was reacted with commercially available 3-methyl-1H-indole-5-carboxylic acid according to general procedure C to afford the title compound as a trifluoroacetic acid salt in 20% yield; $^1$H NMR (DMSO-d$_6$) δ 11.05 (s, 1H), 10.34 (s, 1H), 8.60 (s, 1H), 8.26 (s, 1H), 7.98 (d, J=9 Hz, 1H), 7.75 (d, J=6 Hz, 1H), 7.70 (d, J=6 Hz, 1H), 7.56 (t, J=6 Hz, 1H), 7.41 (d, J=6 Hz, 1H), 7.21 (s, 1H), 2.32 (s, 3H); LCMS (ESI) m/z 319 (MH+).

N-[3-(1H-1,2,3,4-Tetrazol-5-yl)phenyl]-1H-indazole-6-carboxamide (33)

3-(1H-Tetrazol-5-yl)aniline was reacted with commercially available 1H-indazole-6-carboxylic acid according to general procedure C to afford the title compound in 9% yield; $^1$H NMR (DMSO-d$_6$) δ 10.61 (s, 1H), 8.61 (s, 1H), 8.18 (d, J=6 Hz, 2H), 7.96 (d, J=6 Hz, 1H), 7.89 (d, J=9 Hz, 1H), 7.69-7.74 (m, 2H), 7.58 (t, J=6 Hz, 1H); LCMS (ESI) m/z 306 (MH+).

3-Bromo-N-[3-(1H-1,2,3,4-tetrazol-5-yl)phenyl]-1H-indole-5-carboxamide (34)

3-(1H-Tetrazol-5-yl)aniline was reacted with commercially available 3-bromo-1H-indole-5-carboxylic acid according to general procedure C to afford the title compound as a trifluoroacetic acid salt in 3% yield; $^1$H NMR (DMSO-d$_6$) δ 11.77 (s, 1H), 10.50 (s, 1H), 8.60 (s, 1H), 8.19 (s, 1H), 7.98 (d, J=6 Hz, 1H), 7.85 (d, J=9 Hz, 1H), 7.71 (d, J=6 Hz, 1H), 7.68 (d, J=3 Hz, 1H), 7.57 (d, J=6 Hz, 1H), 7.53 (d, J=6 Hz, 1H); LCMS (ESI) m/z 383 (MH+).

Methyl 3-[3-(trifluoromethyl)benzamido]-2,3-dihydro-1H-indene-1-carboxylate (35)

An oven-dried vial charged with methyl 3-amino-2,3-dihydro-1H-indene-1-carboxylate (Ref. Synthesis (2) 239-242, 2001) (135 mg, 0.7 mmol), 3-(trifluoromethyl) benzoic acid (134 mg, 0.7 mmol), O-(7-azabenzotriazol-1-yl)-N,N,N',N'-tetramethyluronium hexafluorophosphate (293 mg, 0.77 mmol) and N,N'-diisopropylethylamine (0.24 mL, 1.4 mmol) in N,N-dimethylformamide (0.5 mL) was stirred at room temperature for 16 h. The reaction mixture was diluted with water (2 mL) and extracted with ethyl acetate. The organic extract was washed with brine, dried over magnesium sulfate and concentrated under reduced pressure. The crude material thus obtained was purified by flash column chromatography (25% ethyl acetate-hexanes) to afford in 3:1 ratio the trans isomer (R$_f$=0.44) and cis isomer (R$_f$=0.28) in an overall yield of 69%. Trans isomer $^1$H NMR (CDCl$_3$) δ 8.13 (s, 1H), 7.95 (d, J=6 Hz, 1H), 7.70-7.76 (m, 2H), 7.52-7.57 (m, 2H), 7.38-7.40 (m, 1H), 7.28-7.31 (m, 2H), 5.75-5.80 (m, 1H), 4.11 (d, J=6 Hz, 1H), 3.77 (s, 3H), 2.68-2.75 (m, 1H), 2.33-2.38 (m, 1H); LCMS (ESI) m/z 364 (MH+). Cis isomer $^1$H NMR (CDCl$_3$) δ 8.02 (s, 1H), 7.96 (d, J=6 Hz, 1H), 7.75 (d, J=6 Hz, 1H), 7.56 (d, J=6 Hz, 1H), 7.30-7.44 (m, 4H), 6.39 (bs, 1H), 5.87-5.93 (m, 1H), 4.20-4.23 (m, 1H), 3.71 (s, 3H), 3.01-3.08 (m, 1H), 2.17-2.24 (m, 1H); LCMS (ESI) m/z 364 (MH+).

N-[(1R,3S)-3-Cyano-2,3-dihydro-1H-inden-1-yl]-3-(trifluoromethyl)benzamide (36)

An oven-dried vial charged with cis isomer of methyl 3-[3-(trifluoromethyl)benzamido]-2,3-dihydro-1H-indene-1-carboxylate (75 mg, 0.21 mmol) and 1M solution of lithium hydroxide in water (0.41 mL, 0.41 mmol) in 2:1 ratio of methanol/water (3 mL) was stirred at 40° C. for an hour. The reaction mixture was adjusted approximately to pH 2 with 1 N HCl and extracted with ethyl acetate. The organic extract was washed with brine, dried over magnesium sulfate and concentrated under reduced pressure to obtain crude (1S,3R)-3-[3-(trifluoromethyl)benzamido]-2,3-dihydro-1H-indene-1-carboxylic acid that was used without further purification.

(1S,3R)-3-[3-(Trifluoromethyl)benzamido]-2,3-dihydro-1H-indene-1-carboxylic acid, di-tert-butyl dicarbonate (60 mg, 0.27 mmol), ammonium bicarbonate (21 mg, 0.27 mmol) and pyridine (2 μL, 0.027) were stirred in acetone (3 mL) at room temperature for 18 h. The reaction mixture was concentrated under reduced pressure and redissolved in ethyl acetate. The organic layer was washed with 0.1 N HCl, water and brine, dried over magnesium sulfate and concentrated under reduced pressure to obtain crude (1 S,3R)-3-[3-(trifluoromethyl)benzamido]-2,3-dihydro-1H-indene-1-carboxamide that was used without further purification.

(1S,3R)-3-[3-(Trifluoromethyl)benzamido]-2,3-dihydro-1H-indene-1-carboxamide (50 mg, 0.14 mmol), trifluoroacetic anhydride (0.08 mL, 0.56 mmol) and pyridine (0.068 ml, 0.84 mmol) in 1,4-dioxane (2 mL) were stirred at room temperature for 3 h. The reaction mixture was diluted with ethyl acetate and washed with water and brine. The organic extract was dried over magnesium sulfate and concentrated under reduced pressure. The crude material thus obtained was purified by flash column chromatography (25% ethyl acetate-hexanes) to afford the title compound in 52% yield. $^1$H NMR (CDCl$_3$) δ 8.07 (s, 1H), 7.97 (d, J=6 Hz, 1H), 7.79 (d, J=6 Hz, 1H), 7.59 (t, J=6 Hz, 1H), 7.52 (d, J=3 Hz, 1H), 7.41-7.44 (m, 3H), 5.73-5.79 (m, 1H), 4.13 (t, J=6 Hz, 1H), 3.13-3.20 (m, 1H), 2.27-2.34 (m, 1H); LCMS (ESI) m/z 331 (MH+).

N-[(1R,3S)-3-(1H-1,2,3,4-Tetrazol-5-yl)-2,3-dihydro-1H-inden-1-yl]-3-(trifluoromethyl)benzamide (37)

An oven-dried vial was charged with N-[(1R,3S)-3-cyano-2,3-dihydro-1H-inden-1-yl]-3-(trifluoromethyl)benzamide (36 mg, 0.11 mmol), sodium azide (14 mg, 2.0 mmol), zinc bromide (12 mg, 0.055 mmol) in a 1:2 mixture of 2-propanol/water (3 mL) was heated to reflux for 18 h. The reaction mixture was cooled, adjusted to pH 2 with 0.1N HCl and extracted with ethyl acetate. The organic extract was dried over magnesium sulfate and concentrated under reduced pressure. The crude material thus obtained was purified by reverse phase HPLC to afford the title compound in 39% yield. $^1$H NMR (DMSO-d$_6$) δ 9.23 (d, J=6 Hz, 1H), 8.30 (s, 1H), 8.25 (d, J=6 Hz, 1H), 7.91 (d, J=6 Hz, 1H), 7.73 (t, J=6 Hz, 1H), 7.26-7.29 (m, 3H), 5.70-5.74 (m, 1H), 4.79 (t, J=6 Hz, 1H), 2.93-2.98 (m, 1H), 2.21-2.30 (m, 1H); LCMS (ESI) m/z 374 (MH+).

N-[3-(Methanesulfonylcarbamoyl)phenyl]-3-(trifluoromethyl)benzamide (38)

An oven-dried vial charged with 3-(trifluoromethyl) benzoic acid (0.1 g, 0.52 mmol) in dichloromethane (5.0 ml) was cooled to 0° C. 1-Chloro-N,N,2-trimethyl-1-propenylamine (0.077 mL, 0.58 mmol) was added to the reaction mixture and stirred at 0° C. for 30 min. 3-Aminobenzoic acid (71 mg, 0.52 mmol) and N,N'-diisopropylethylamine (0.18 mL, 1.04 mmol) were then added to the reaction mixture and stirred at room temperature for 2 h. The reaction mixture was washed with sat. NaHCO$_3$, the aqueous phase adjusted approximately to pH 2 with 1 N HCl. and extracted with ethyl acetate. The ethyl acetate extract was dried over magnesium sulfate and concentrated under reduced pressure. The crude 3-[3-(trifluoromethyl)benzamido]benzoic acid thus obtained was used without further purification.

3-[3-(Trifluoromethyl)benzamido]benzoic acid (30 mg, 0.097 mmol) and 1,1'-carbonyldiimidazole (31 mg, 0.194 mmol) in tetrahydrofuran (2.0 mL) were stirred at room temperature for 90 min. Methanesulfonamide (14 mg, 0.145 mmol) and 1,8-diazabicyclo[5.4.0]undec-7-ene (0.022 mL, 0.145 mmol) were added and the mixture was stirred at room temperature for 18 h. The reaction mixture was diluted with ethyl acetate and washed with 1 N HCl, water and brine. The organic extract was dried over magnesium sulfate and concentrated under reduced pressure. The crude material thus obtained was purified by reverse phase HPLC to afford the title compound in 14% yield. $^1$H NMR (DMSO-d$_6$) δ 10.64 (s, 1H), 8.31 (s, 2H), 8.26 (d, J=6 Hz, 1H), 8.03 (d, J=6 Hz, 1H), 7.96 (d, J=6 Hz, 1H), 7.78 (t, J=6 Hz, 1H), 7.68 (d, J=6 Hz, 1H), 7.50 (t, J=6 Hz, 1H), 3.35 (s, 3H); LCMS (ESI) m/z 387 (MH+).

N-{3-[(Benzyloxy)carbamoyl]phenyl}-3-(trifluoromethyl)benzamide (39)

An oven-dried vial charged with methyl 3-aminobenzoate (90 mg, 0.6 mmol), 3-(trifluoromethyl) benzoic acid (113 mg, 0.6 mmol), O-(7-azabenzotriazol-1-yl)-N,N,N',N'-tetramethyluronium hexafluorophosphate (250 mg, 0.66 mmol) and N,N'-diisopropylethylamine (0.2 mL, 1.2 mmol) in N,N-dimethylformamide (0.5 mL) was stirred at room temperature for 18 h. The reaction mixture was diluted with water (2 mL) and extracted with ethyl acetate. The organic extract was washed with water, brine, dried over magnesium sulfate and concentrated under reduced pressure. The crude methyl 3-[3-(trifluoromethyl)benzamido]benzoate was used without further purification.

An oven-dried flask was charged with methyl 3-[3-(trifluoromethyl)benzamido]benzoate (20 mg, 0.062 mmol) and O-benzylhydroxylamine hydrochloride (10 mg, 0.062 mmol) in tetrahydrofuran (2 mL) and stirred at −78° C. After adding 1 M solution of lithium bis(trimethylsilyl)amide in tetrahydrofuran (0.19 mL, 0.19 mmol) and stirring at −78° C. for an additional 10 min, the reaction mixture was warmed up to room temperature. The reaction mixture was quenched with saturated NH$_4$Cl and extracted with ethyl acetate. The organic extract was washed with water, brine, dried over magnesium sulfate and concentrated under reduced pressure. The crude material thus obtained was purified by flash column chromatography (40% ethyl acetate-hexanes) to afford the title compound in 40% yield. $^1$H NMR (CDCl$_3$) δ 8.19 (s, 1H), 8.11 (d, J=6 Hz, 1H), 7.87 (d, J=6 Hz, 2H), 7.78 (d, J=6 Hz, 2H), 7.61 (t, J=6 Hz, 1H), 7.34-7.45 (m, 7H), 5.00 (s, 2H); LCMS (ESI) m/z 415 (MH+).

N-[3-(Hydroxycarbamoyl)phenyl]-3-(trifluoromethyl)benzamide (40)

A solution of N-{3-[(Benzyloxy)carbamoyl]phenyl}-3-(trifluoromethyl)benzamide (20 mg, 0.048 mmol) in methanol was passed through a Pd/C cartridge (10 wt %) at a flow rate of 1 mL/min using the H-Cube hydrogenation system. The solution was concentrated under reduced pressure and purified by reverse phase HPLC to obtain the title compound in 41% yield. $^1$H NMR (DMSO-d$_6$) δ 8.19 (s, 1H), 8.11 (s, 1H), 7.85 (d, J=6 Hz, 2H), 7.78 (d, J=6 Hz, 1H), 7.61 (t, J=6 Hz, 1H), 7.52 (s, 1H), 7.41 (t, J=6 Hz, 1H); LCMS (ESI) m/z 325 (MH+).

N-(3-Nitrophenyl)-3-(trifluoromethyl)benzamide (41)

An oven-dried vial charged with 3-nitroaniline (100 mg, 0.72 mmol), 3-(trifluoromethyl) benzoic acid (138 mg, 0.72 mmol), O-(7-azabenzotriazol-1-yl)-N,N,N',N'-tetramethyluronium hexafluorophosphate (300 mg, 0.79 mmol) and N,N'-diisopropylethylamine (0.25 mL, 1.44 mmol) in N,N-dimethylformamide (2 mL) was stirred at room temperature for 18 h. The reaction mixture was diluted with water (5 mL) and extracted with ethyl acetate. The organic extract was washed with water, brine, dried over magnesium sulfate and concentrated under reduced pressure. The crude material thus obtained was purified by flash column chromatography (30% ethyl acetate-hexanes) to obtain 45% yield. $^1$H NMR (CDCl$_3$) δ 8.38 (s, 1H), 8.30 (d, J=6 Hz, 2H), 8.03-8.14 (m, 2H), 7.67 (d, J=6 Hz, 1H), 7.55-7.69 (m, 3H); LCMS (ESI) m/z 311 (MH+).

N-[3-(Methylsulfonylcarbamoylamino)phenyl]-3-(trifluoromethyl)benzamide (42)

A solution of N-(3-nitrophenyl)-3-(trifluoromethyl)benzamide (100 mg, 0.32 mmol) in methanol was passed through a Pd/C cartridge (10 wt %) at a flow rate of 1 mL/min using the H-Cube hydrogenation system. The solution was concentrated under reduced pressure to obtain crude N-(3-aminophenyl)-3-(trifluoromethyl)benzamide that was used without further purification.

An oven-dried vial charged with N-(3-aminophenyl)-3-(trifluoromethyl)benzamide (25 mg, 0.089 mmol), p-nitrophenylchloroformate (20 mg, 0.098 mmol) and pyridine (8 μL, 0.098 mmol) in dichloromethane (2 mL) was stirred at room temperature for 2 h. Methanesulfonamide (17 mg, 0.178 mmol) and triethylamine (0.062 mL, 0.44 were) added to the reaction mixture and stirred at room temperature for 18 h. The reaction mixture was diluted with dichloromethane and washed with 0.1 N HCl, water and brine. The organic layer was dried over magnesium sulfate and concentrated under reduced pressure. The crude material thus obtained was purified by flash column chromatography to afford the title compound in 14% yield. $^1$H NMR (DMSO-d$_6$) δ 10.46 (s, 1H), 8.89 (s, 1H), 8.26 (s, 1H), 8.23 (d, J=6 Hz, 1H), 7.94 (d, J=6 Hz, 2H), 7.76 (t, J=6 Hz, 1H), 7.46 (d, J=6 Hz, 1H), 7.26 (t, J=6 Hz, 1H), 7.15 (d, J=6 Hz, 1H), 1.20 (s, 3H); LCMS (ESI) m/z 402 (MH+).

Protein Purification, Crystallization and Structure Determination

CTX-M-9, a class A β-lactamase that we have previously studied, was used to represent the CTX-M family. The protein was purified as previously described[31] and crystallized in 1.2-1.6M potassium phosphate buffer (pH 8.3) from hanging drops at 20° C. The final concentration of the protein in the drop ranged from 6.5 mg ml$^{-1}$ to 9 mg ml$^{-1}$. The complex crystals were obtained through soaking methods. Based on the variability in terms of solubility and affinity, compound soaking times varied considerably, from 1 hour to 24 hours. Diffraction was measured at three beamlines: X6A at National Synchrotron Light Source, Brookhaven, N.Y.; 23-ID-B of GM/CA CAT at Advanced Photon Source (APS), Argonne, Illinois, and 8.3.1, Advanced Light Source (ALS), Berkeley, Calif. Data was processed with HKL2000[32]. The models for Refinement were obtained through first using a rigid-body refinement using Refmac in CCP4[33] with an apo CTX-M-9 structure. CCP4 and Coot[34] were used to complete the model rebuilding and refinement.

Inhibition Assays

The hydrolysis reaction of CTX-M activity was measured using the β-lactam substrate nitrocefin in 100 mM Tris-HCl (pH 7.0, with 0.01% v/v Triton X-100) and monitored using an Hewlett-Packard spectrophotometer at 480 nM wavelength. Nitrocefin was 50 μM in the inhibition assays. The K$_m$ of nitrocefin for CTX-M was determined to be 24 μM. The compounds were synthesized as previously described or purchased from the company Chembridge, and assayed without further purification. The highest concentrations at which the compounds were tested were up to 1-3 mM (depending on their solubility) in IC$_{50}$ experiment. The reaction was initiated by adding protein to the reaction buffer last.

REFERENCES, EACH OF WHICH IS INCORPORATED HEREIN BY REFERENCE

1. Chen, Y.; Zhang, W.; Shi, Q.; Hesek, D.; Lee, M.; Mobashery, S.; Shoichet, B. K. Crystal structures of penicillin-binding protein 6 from *Escherichia coli*. *J Am Chem Soc* 2009, 131, 14345-54.

2. Tipper, D. J.; Strominger, J. L. Mechanism of action of penicillins: a proposal based on their structural similarity to acyl-D-alanyl-D-alanine. *Proc Natl Acad Sci USA* 1965, 54, 1133-41.
3. Silvaggi, N. R.; Anderson, J. W.; Brinsmade, S. R.; Pratt, R. F.; Kelly, J. A. The crystal structure of phosphonate-inhibited D-Ala-D-Ala peptidase reveals an analogue of a tetrahedral transition state. *Biochemistry.* 2003, 42, 1199-208.
4. Frere, J. M. Beta-lactamases and bacterial resistance to antibiotics. *Mol Microbiol* 1995, 16, 385-95.
5. Taubes, G. The bacteria fight back. *Science* 2008, 321, 356-61.
6. Bush, K.; Jacoby, G. A.; Medeiros, A. A. A functional classification scheme for beta-lactamases and its correlation with molecular structure. *Antimicrob Agents Chemother* 1995, 39, 1211-33.
7. Livermore, D. M. beta-Lactamases in laboratory and clinical resistance. *Clin Microbiol Rev* 1995, 8, 557-84.
8. Chen, Y.; Delmas, J.; Sirot, J.; Shoichet, B.; Bonnet, R. Atomic resolution structures of CTX-M beta-lactamases: extended spectrum activities from increased mobility and decreased stability. *J Mol Biol* 2005, 348, 349-62.
9. Chen, Y.; Shoichet, B.; Bonnet, R. Structure, function, and inhibition along the reaction coordinate of CTX-M beta-lactamases. *J Am Chem Soc* 2005, 127, 5423-34.
10. Bonnet, R. Growing group of extended-spectrum beta-lactamases: the CTX-M enzymes. *Antimicrob Agents Chemother* 2004, 48, 1-14.
11. Bradford, P. A. Extended-spectrum beta-lactamases in the 21st century: characterization, epidemiology, and detection of this important resistance threat. *Clin Microbiol Rev* 2001, 14, 933-51.
12. Delmas, J.; Leyssene, D.; Dubois, D.; Birck, C.; Vazeille, E.; Robin, F.; Bonnet, R. Structural insights into substrate recognition and product expulsion in CTX-M enzymes. *J Mol Biol* 400, 108-20.
13. Drawz, S. M.; Bonomo, R. A. Three decades of beta-lactamase inhibitors. *Clin Microbiol Rev* 2010, 23, 160-201.
14. Bennett, P. M.; Chopra, I. Molecular basis of beta-lactamase induction in bacteria. *Antimicrob Agents Chemother* 1993, 37, 153-8.
15. Jacobs, C.; Frere, J. M.; Normark, S. Cytosolic intermediates for cell wall biosynthesis and degradation control inducible beta-lactam resistance in gram-negative bacteria. *Cell* 1997, 88, 823-832.
16. Petrosino, J.; Cantu, C., 3rd; Palzkill, T. beta-Lactamases: protein evolution in real time. *Trends Microbiol* 1998, 6, 323-7.
17. Pages, J. M.; Lavigne, J. P.; Leflon-Guibout, V.; Marcon, E.; Bert, F.; Noussair, L.; Nicolas-Chanoine, M. H. Efflux pump, the masked side of beta-lactam resistance in *Klebsiella pneumoniae* clinical isolates. *PLoS ONE* 2009, 4, e4817.
18. Chen, Y.; Shoichet, B. K. Molecular docking and ligand specificity in fragment-based inhibitor discovery. *Nat Chem Biol* 2009, 5, 358-64.
19. Payne, D. J.; Gwynn, M. N.; Holmes, D. J.; Pompliano, D. L. Drugs for bad bugs: confronting the challenges of antibacterial discovery. *Nat Rev Drug Discov.* 2007, 6, 29-40.
20. Renslo, A. R. Antibacterial oxazolidinones: emerging structure-toxicity relationships. *Expert Rev Anti Infect Ther* 2010, 8, 565-74.
21. Chen, Y.; Bonnet, R.; Shoichet, B. K. The acylation mechanism of CTX-M beta-lactamase at 0.88 a resolution. *J Am Chem Soc.* 2007, 129, 5378-80.
22. Lorber, D. M.; Shoichet, B. K. Hierarchical docking of databases of multiple ligand conformations. *Curr Top Med Chem.* 2005, 5, 739-49.
23. Irwin, J. J.; Shoichet, B. K. ZINC—a free database of commercially available compounds for virtual screening. *J Chem Inf Model.* 2005, 45, 177-82.
24. Ryckmans, T.; Edwards, M. P.; Horne, V. A.; Correia, A. M.; Owen, D. R.; Thompson, L. R.; Tran, I.; Tutt, M. F.; Young, T. Rapid assessment of a novel series of selective CB2 agonists using parallel synthesis protocols: A Lipophilic Efficiency (LipE) analysis. *Bioorganic & Medicinal Chemistry Letters* 2009, 19, 4406-4409.
25. Ibuka, A. S.; Ishii, Y.; Galleni, M.; Ishiguro, M.; Yamaguchi, K.; Frere, J. M.; Matsuzawa, H.; Sakai, H. Crystal structure of extended-spectrum beta-lactamase Toho-1: insights into the molecular mechanism for catalytic reaction and substrate specificity expansion. *Biochemistry* 2003, 42, 10634-43.
26. Shimamura, T.; Ibuka, A.; Fushinobu, S.; Wakagi, T.; Ishiguro, M.; Ishii, Y.; Matsuzawa, H. Acyl-intermediate structures of the extended-spectrum class A beta-lactamase, Toho-1, in complex with cefotaxime, cephalothin, and benzylpenicillin. *J Biol Chem* 2002, 277, 46601-8.
27. Tomanicek, S. J.; Blakeley, M. P.; Cooper, J.; Chen, Y.; Afonine, P. V.; Coates, L. Neutron diffraction studies of a class A beta-lactamase Toho-1 E166A/R274N/R276N triple mutant. *J Mol Biol* 396, 1070-80.
28. Wang, X.; Minasov, G.; Shoichet, B. K. Evolution of an antibiotic resistance enzyme constrained by stability and activity trade-offs. *J Mol Biol* 2002, 320, 85-95.
29. Ke, W.; Sampson, J. M.; Ori, C.; Prati, F.; Drawz, S. M.; Bethel, C. R.; Bonomo, R. A.; van den Akker, F. Novel insights into the mode of inhibition of class A SHV-1 beta-lactamases revealed by boronic acid transition state inhibitors. *Antimicrob Agents Chemother* 55, 174-83.
30. Makovec, F.; Penis, W.; Revel, L.; Giovanetti, R.; Redaelli, D.; Rovati, L. C. Antiallergic and cytoprotective activity of new N-phenylbenzamido acid derivatives. *J Med Chem* 1992, 35, 3633-40.
31. Chen, Y.; Delmas, J.; Sirot, J.; Shoichet, B.; Bonnet, R. Atomic resolution structures of CTX-M beta-lactamases: extended spectrum activities from increased mobility and decreased stability. *J Mol Biol* 2005, 348, 349-62.
32. Otwinowski, Z.; Minor, W. Processing of X-ray diffraction data collected in oscillation mode. *Methods in Enzymology* 1997, 276, 307-326.
33. Collaborative Computational Project, N. The CCP4 suite: programs for protein crystallography. *Acta Crystallogr D Biol Crystallogr* 1994, 50, 760-763.
34. Emsley, P.; Cowtan, K. Coot: model-building tools for molecular graphics. *Acta Crystallogr D Biol Crystallogr.* 2004, 60, 2126-32.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. In an embodiment, the term "about" can include traditional rounding according to significant figures of the numerical value. In addition, the phrase "about 'x' to 'y'" includes "about 'x' to about 'y'".

Many variations and modifications may be made to the above-described embodiments. All such modifications and variations are intended to be included herein within the scope of this disclosure and protected by the following claims.

We claim:

1. A composition, comprising a beta-lactamase inhibitor selected from the group consisting of
   3-cyclopropyl-N-[3-(1H-tetrazol-5-yl)-phenyl]-benzamide;
   3-(2-pyrimidyl)-N-[3-(1H-tetrazol-5-yl)-phenyl]-benzamide;
   N-(3-(1H-tetrazol-5-yl)phenyl)-3-((dimethylamino)methyl)benzamide;
   1H-indole-4-carboxylic acid [3-(1H-tetrazol-5-yl)-phenyl]-amide;
   3H-benzoimidazole-4-carboxylic acid [3-(1H-tetrazol-5-yl)-phenyl]-amide;
   1H-indole-5-carboxylic acid [3-(1H-tetrazol-5-yl)-phenyl]-amide;
   1H-indazole-5-carboxylic acid [3-(1H-tetrazol-5-yl)-phenyl]-amide
   3-bromo-5-hydroxy-N-[3-(1H-tetrazol-5-yl)-phenyl]-benzamide;
   3-hydroxy-N-[3-(1H-tetrazol-5-yl)-phenyl]-5-trifluoromethyl-benzamide;
   3-amino-N-[3-(1H-tetrazol-5-yl)-phenyl]-5-trifluoromethyl-benzamide;
   6-fluoro-3H-benzoimidazole-4-carboxylic acid [3-(1H-tetrazol-5-yl)-phenyl]-amide;
   3-bromo-5-cyano-N-[3-(1H-tetrazol-5-yl)-phenyl]-benzamide;
   3-(4-methylphenyl)-N-[3-(1H-1,2,3,4-tetrazol-5-yl)phenyl]-1H-pyrazole-5-carboxamide;
   3-phenyl-N-[3-(1H-1,2,3,4-tetrazol-5-yl)phenyl]-1,2-oxazole-5-carboxamide;
   1-phenyl-N-[3-(1H-1,2,3,4-tetrazol-5-yl)phenyl]-1H-imidazole-4-carboxamide;
   1-phenyl-N-[3-(1H-1,2,3,4-tetrazol-5-yl)phenyl]-1H-imidazole-5-carboxamide;
   3-methyl-N-[3-(1H-1,2,3,4-tetrazol-5-yl)phenyl]-1H-indole-5-carboxamide;
   N-[3-(1H-1,2,3,4-tetrazol-5-yl)phenyl]-1H-indazole-6-carboxamide;
   3-bromo-N-[3-(1H-1,2,3,4-tetrazol-5-yl)phenyl]-1H-indole-5-carboxamide;
   N-[(1R,3S)-3-(1H-1,2,3,4-tetrazol-5-yl)-2,3-dihydro-1H-inden-1-yl]-3-(trifluoromethyl)benzamide and
   N-((1R,3S)-3-(1H-tetrazol-5-yl)-2,3-dihydro-1H-inden-1-yl)-3-fluorobenzamide,
   or salt thereof.

2. The composition of claim 1, further comprising an antibiotic.

3. The composition of claim 2, wherein the antibiotic is a beta-lactam antibiotic.

4. The composition of claim 1, wherein the beta-lactamase inhibitor is selected from the group consisting of
   1H-indazole-5-carboxylic acid [3-(1H-tetrazol-5-yl)-phenyl]-amide; and
   3-Hydroxy-N-[3-(1H-tetrazol-5-yl)-phenyl]-5-trifluoromethyl-benzamide,
   or salt thereof.

5. The composition of claim 1, wherein the beta-lactamase inhibitor is selected from the group consisting of
   N-((1R, 3 S)-3-(1H-tetrazol-5-yl)-2,3-dihydro-1H-inden-1-yl)-3-fluorobenzamide,
   or salt thereof.

6. A pharmaceutical composition comprising a therapeutically effective amount of a beta-lactamase inhibitor selected from the group consisting of
   3-cyclopropyl-N-[3-(1H-tetrazol-5-yl)-phenyl]-benzamide;
   3-(2-pyrimidyl)-N-[3-(1H-tetrazol-5-yl)-phenyl]-benzamide;
   N-(3-(1H-tetrazol-5-yl)phenyl)-3-((dimethylamino)methyl)benzamide;
   1H-indole-4-carboxylic acid [3-(1H-tetrazol-5-yl)-phenyl]-amide;
   3H-benzoimidazole-4-carboxylic acid [3-(1H-tetrazol-5-yl)-phenyl]amide;
   1H-indole-5-carboxylic acid [3-(1H-tetrazol-5-yl)-phenyl]-amide;
   1H-indazole-5-carboxylic acid [3-(1H-tetrazol-5-yl)-phenyl]-amide
   3-bromo-5-hydroxy-N-[3-(1H-tetrazol-5-yl)-phenyl]-benzamide;
   3-hydroxy-N-[3-(1H-tetrazol-5-yl)-phenyl]-5-trifluoromethyl-benzamide;
   3-amino-N-[3-(1H-tetrazol-5-yl)-phenyl]-5-trifluoromethyl-benzamide;
   6-fluoro-3H-benzoimidazole-4-carboxylic acid [3-(1H-tetrazol-5-yl)-phenyl]-amide;
   3-bromo-5-cyano-N-[3-(1H-tetrazol-5-yl)-phenyl]-benzamide;
   3-(4-methylphenyl)-N-[3-(1H-1,2,3,4-tetrazol-5-yl)phenyl]-1H-pyrazole-5-carboxamide;
   3-phenyl-N-[3-(1H-1,2,3,4-tetrazol-5-yl)phenyl]-1,2-oxazole-5-carboxamide;
   1-phenyl-N-[3-(1H-1,2,3,4-tetrazol-5-yl)phenyl]-1H-imidazole-4-carboxamide;
   1-phenyl-N-[3-(1H-1,2,3,4-tetrazol-5-yl)phenyl]-1H-imidazole-5-carboxamide;
   3-methyl-N-[3-(1H-1,2,3,4-tetrazol-5-yl)phenyl]-1H-indole-5-carboxamide;
   N-[3-(1H-1,2,3,4-tetrazol-5-yl)phenyl]-1H-indazole-6-carboxamide;
   3-bromo-N-[3-(1H-1,2,3,4-tetrazol-5-yl)phenyl]-1H-indole-5-carboxamide;
   N-[(1R,3S)-3-(1H-1,2,3,4-tetrazol-5-yl)-2,3-dihydro-1H-inden-1-yl]-3-(trifluoromethyl)benzamide; and
   N-((1R,3S)-3-(1H-tetrazol-5-yl)-2,3-dihydro-1H-inden-1-yl)-3-fluorobenzamide,
   or a pharmaceutically acceptable salt of the beta-lactamase inhibitor, and a pharmaceutically acceptable carrier, to treat a condition.

7. The pharmaceutical composition of claim 6, further comprising an antibiotic.

8. The pharmaceutical composition of claim 7, wherein the antibiotic is a beta-lactam antibiotic.

9. The pharmaceutical composition of claim 6, wherein the beta-lactamase inhibitor is selected from the group consisting of
   1H-indazole-5-carboxylic acid [3-(1h-tetrazol-5-yl)-phenyl]-amide, and
   3-Hydroxy-N-[3-(1H-tetrazol-5-yl)-phenyl]-5-trifluoromethyl-benzamide,
   or a pharmaceutically acceptable salt thereof.

10. The pharmaceutical composition of claim 6, wherein the beta-lactamase inhibitor is selected from the group consisting of
N-((1R,3S)-3-(1H-tetrazol-5-yl)-2,3-dihydro-1H-inden-1-yl)-3-fluorobenzamide,
or a pharmaceutically acceptable salt thereof.

\* \* \* \* \*